(12) United States Patent
Blaser et al.

(10) Patent No.: US 6,570,004 B1
(45) Date of Patent: May 27, 2003

(54) **DAPE GENE ON *HELICOBACTER PYLORI* AND DAPE⁻ MUTANT STRAINS OF *HELICOBACTER PYLORI***

(75) Inventors: Martin J. Blaser, Nashville, TN (US); Mikio Karita, Hofu (JP)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/331,568

(22) PCT Filed: Dec. 23, 1997

(86) PCT No.: PCT/US97/24147

§ 371 (c)(1),
(2), (4) Date: Dec. 9, 1999

(87) PCT Pub. No.: WO98/27819

PCT Pub. Date: Jul. 2, 1998

Related U.S. Application Data

(60) Provisional application No. 60/033,824, filed on Dec. 23, 1996.

(51) Int. Cl.[7] .............................................. C07H 21/04
(52) U.S. Cl. ....................... 536/23.2; 514/44; 435/69.1; 435/252.3
(58) Field of Search ........................ 514/44; 536/23.2; 435/252.3, 69.1

(56) References Cited

U.S. PATENT DOCUMENTS 5,919,462 A * 7/1999 Narwa et al. ............ 424/208.1

FOREIGN PATENT DOCUMENTS

| WO | 95/14772 | * 6/1995 | |
| WO | 96/40893 | * 12/1996 | ............ C12N/15/00 |

OTHER PUBLICATIONS

Karita, M. et al., Characterization of *Helicobacter pylori* dapE and construction of a conditionally lethal dapE mutant, *Infection and Immunity*, 1997, vol. 65, No. 10 pp. 4158–4164.

* cited by examiner

*Primary Examiner*—Lynette R. F. Smith
*Assistant Examiner*—Ginny Allen Portner
(74) *Attorney, Agent, or Firm*—Needle & Rosenberg, P.C.

(57) ABSTRACT

The invention provides the dapE gene of *Helicobacter pylori* and *H. pylori* dapE⁻ mutants and to methods of using the mutants to express foreign genes and immunize against foreign agents. The dapE gene can consist of the nucleotide sequence defined in SEQ ID NO:3. Nucleic acids of the gidA gene and ORF 2 of *H. pylori* are provided. Examples of these nucleic acids can be found in SEQ ID NO:1 and SEQ ID NO:5, respectively. Having provided these nucleic acids, hybridizing nucleic acids in accord with the description of hybridizing nucleic acids of dapE are also provided.

13 Claims, 12 Drawing Sheets

```
  1 aat tcc cta tca tga aac cta aaa tca atc tcc tag ggc ttg tgc cta cta gta aat aat   60
    tta agg gat agt act ttg gat ttt agt tag agg atc ccg aac ccg aac atc tgc cta gat cat tta tta   142
161                    N    G     I    M     F     L     I     L     R     P     S     T     G     V     L     I     L    I 61 gct taa agc gat gcg cgt gtg caa gtt cca ttt cat gct taa agc taa aat tta aaa ccc   120
    cga att tcg cta cgc gca cac gtt caa ggt aaa ttt aac cat gct taa agt tcg att ttt ggg   122
141                    S     L     A     I     R     T     H     L     Q     P     F     M     S     L     A     I     F    G 121 tcc cat aaa aag aaa gat gat cgg aat cga tgc gta cga aga aga aga tct tcg gac gct agc gaa ttg atc   180
    agg gta ttt ttc tta gcc cta tta gcc gct cga cgt gca cat acg tct tct cga cga ctg cag aac tag cgt taa   182
121                    G     M     F     L     F     I     P     S     A     Y     M     S     S     S     V     A     F    D 181 cac gct aaa gac gct cac caa aag cac caa agg taa att aac cgc agc cac ccc agg cag ttg atc aat ggt   240
    gtg cga ttt ctg cga gtg gtt ttc gtg gtt tcc att taa ttg gcg tcg gtg ggg tcc gtc aac tta cca   102
101                    V     S     F     L     V     Q     H     P     A     T     L     R     G     A     V     P     L    D    I 241 ttc tgt cat cca tat ccc cat taa aac agc ttc ttc tac aat atg tcc tat taa ccc ctt cgc ctt   300
    aag aca gta ggt ata ggg gta att ttg tcg aag aag atg tta tac agg ata att ggg gaa gcg gaa   62
 81                    E     T     M     W     I     G     K     V     A     E     F     V     I     H     Y     P     L    Q    K 301 ata att taa gat ggt att aag gat ctt ggg gat cta cca att cgc taa caa tta aac tct gcg   360
    tat taa att cta cca tcc tta gaa cca cta gat ggt taa gcg att gtt aac atg att tga   42
 61                    Y     N     L     S     I     M     P     L     K     P     I     V     G     I     H     Q     L    N    S 361 cgc aca gat aat aag cgc ttc gcg cta atg cgc att gtt cac gtg cac gat att gag   420
    gcg tgt cta tta ttc gcg aag cgc gat tac gcg taa caa gtg cac gtg cta taa ctc   22
 41                    A     Y     I     I     L     A     R     D     V     T     V     G     L     H     V     I    E 421 ctt agt gct ttt atc ggt gcg cgt atc ggt atg cga atg att ttc   480
    gaa tca cga aaa tag cca cgc gca tag cca tag cct tac gct taa aag   2
 21                    K     T     S     K     D     D     R     T     H     N     A     S     H     V     I    F    E
                              -10                                                                       -35
```

FIG.2

```
481 cattttatttttaccctttaaaattactaacctccatgctacaataaaacgttttcaaaactaagatttagaaaatca   560
    gta
      M
    1  S.D.

561 tatcaaaacaggaaaaga GTG GTA AAA GAA AGT GAT ATT TTA GTG ATT GGT GGG CAT GCG   624
                       M   V   K   E   S   D   I   L   V   I   G   G   H   A
                       1                                                   15

625 GGC ATT GAA GCG AGC TTG ATT GCA GCC AAA ATG GGG GCT GTG CAT TTA ATC ACC ATG   684
     G   I   E   A   S   L   I   A   A   K   M   G   A   V   H   L   I   T   M
    16                                                                      35

685 CTC ATA GAC ACG ATC GGT TTA GCG AGC TGT AAC CCG AGC ATT GGG GGC TTG GGT AAA GGG   744
     L   I   D   T   I   G   L   A   S   C   N   P   S   I   G   G   L   G   K   G
    36                                                                          55

745 CAT TTG ACT AAA GAA GTG GAT GTT TTA AAC GTG TTA ATG GGG GCT ATT ATT ACA GAT CAT AGC   804
     H   L   T   K   E   V   D   V   L   N   V   L   M   G   A   I   I   T   D   H   S
    56                                                                              75

805 GGT TTG CAA TAT CGT GAT ACT TAC TGT AAA GCT TCT AAA GCG AGA AAT CTT GTT TTA AGG GCG   864
     G   L   Q   Y   R   D   T   Y   C   K   A   S   K   G   R   N   L   V   L   R   A
    76                                                                              95

865 CAA ATT GAT ATG GAT ACT CAA GAA ATG ACC ACT TAC AGA GCT GAG CAC CAA AAC GAT GAG GTA GGC   924
     Q   I   D   M   D   T   Q   E   M   T   T   Y   R   A   E   H   Q   N   D   E   V   G
    96                                                                                  115

925 TTG AGC GTC TCT CAA ATT AAT AAC ATT AAT TAC AGA GCT GAG CAC CAA AAC CAA GTG ATC ATC ACC   984
     L   S   V   S   Q   I   N   N   I   N   Y   R   A   E   H   Q   N   Q   V   I   I   T
    116                                                                                 135

985 GTA ACC ACG AAC ATT AAT GGG GTG CAT ATT GGC CAT GTG CAT CAA CAA AAC GGG CGT TTT GGG GAA   1049
     V   T   T   N   I   N   G   V   H   I   G   H   V   H   Q   Q   N   G   R   F   G   E
    136                                                                                 155

1045 TTT TTA AAA ACG AAC ATT AAT GGG CAT GTG CAT CAA CAA AAC GGG CGT TTT GGG GAA   1104
      F   L   K   T   N   I   N   G   H   V   H   Q   Q   N   G   R   F   G   E
    156                                                                       175

1105 AAC GCT TCC AAT TCT TTA GCC TTG AAT TTA AGG GAG CTT GGC TTT AAG GTG GAG AGG TTA   1164
      N   A   S   N   S   L   A   L   N   L   R   E   L   G   F   K   V   E   R   L
    176                                                                           195
```

FIG. 2 Cont.1

```
1165 AAA ACC GGC ACT TGC CCA AGA GTG GCC GGC AAT AGC ATT GAT TTT GAA GGC TTA GAA GAG 1229
 196  K   T   G   T   C   P   R   V   A   G   N   S   I   D   F   E   G   L   E   E  215

1225 CAT TTT GGG GAT GCA AAC CCT ACT TAC TAT CCC TAT TTC AGC TAT AAA GAT TTT AAC CCC ACC 1284
 216  H   F   G   D   A   N   P   T   Y   Y   P   Y   F   S   Y   K   D   F   N   P   T  235

1285 CAA CTC TCT TGT TTC ATC ACT TAC ACT AAC CCC ATT ACC CAA ATC ATT AGG GAT AAT 1344
 236  Q   L   S   C   F   I   T   Y   T   N   P   I   T   Q   I   I   R   D   N  255

1345 TTC CAC CGA GCT CCC CTT TTT AGC GGT CAA ATT GAA CAC CAC CAA GGC CCA AGG TAT TGC CCT 1404
 256  F   H   R   A   P   L   F   S   G   Q   I   E   H   H   Q   G   P   R   Y   C   P  275

1405 AGC ATT GAA GAT AAA ATT CAT AAA AAC CGC AGT GAA AAA ATA CGC CAG CTG TTT TTA GAG 1464
 276  S   I   E   D   K   I   H   K   N   R   S   E   K   I   R   Q   L   F   L   E  295

1465 CCT CAA ACC ATT CAT AAA GAA AAG GTC TAT ATC TAT TAT ATC AAC GGC TTA AGC ACC TCT TTG CCC CTA 1524
 296  P   Q   T   I   H   K   E   K   V   Y   I   Y   Y   I   N   G   L   S   T   S   L   P   L  315

1525 GAT GTG CAA GAA GAT AAA GGG ATA GAG TAT GAT TTC ATC AAA GGC TTA GAA AAC GCC CTC ATC ACG CGC 1584
 316  D   V   Q   E   D   K   G   I   E   Y   D   F   I   K   G   L   E   N   A   L   I   T   R  335

1585 TAT GGC ATA GCG AAA GGG CTT TAT GAT TTG CTT ATG GCT GGG CAA ATC CAG CCT ACA GAA TTA ACC CAC GCT 1644
 336  Y   G   I   A   K   G   L   Y   D   L   L   M   A   G   Q   I   Q   P   T   E   L   T   H   A  355

1645 ACC AAA AAA ATC AAA GAT CAA CAA GGG CTT ATG GCT GGG CAA ATC AAT GGG ACT GCC TAT GAA 1704
 356  T   K   K   I   K   D   Q   Q   G   L   M   A   G   Q   I   N   G   T   A   Y   E  375

1705 GAA GCG GCG GAT CAA GGG CTT ATG GCT AAT GCG ATT AAT GCG GTA TTA GCC TTA AAG AAT CAA 1764
 376  E   A   A   D   Q   G   L   M   A   N   A   I   N   A   V   L   A   L   K   N   Q  395

1765 GCC CCC TTT ATT TTA AAG CGC AAT GAA GCT TAT ATT GGC GTT TTG ATT GAT GAT TTG GTT 1824
 396  A   P   F   I   L   K   R   N   E   A   Y   I   G   V   L   I   D   D   L   V  415
```

FIG.2 Cont.2

```
1825 ACT AAA GGC ACG AAT GAG CCT TAC AGA ATG TTT ACT AGC CGA GCC GAA TAC CGC TTG CTT 1884
 416  T   K   G   T   N   E   P   Y   R   M   F   T   S   R   A   E   Y   R   L   L   435

1885 TTA AGA GAG GAC AAC ACG CTT TTT AGG TTG GGC GAA CAT GCC TAT CGT TTA GGG CTT ATG 1944
 436  L   R   E   D   N   T   L   F   R   L   G   E   H   A   Y   R   L   G   L   M   455

1945 GAA CAG GAT TTT TAT AAG GAA TTA AAA GAT AAA CAA GAG ATA CAA GAC AAT CTC AAA 2009
 956  E   Q   D   F   Y   K   E   L   K   D   K   Q   E   I   Q   D   N   L   K   975

2005 CGC CTT AAA GAA TGC GTC CTT ACC CCT AGT AAA AAA TTG TTA AAA CGC TTG AAC GAA TTA 2069
 476  R   L   K   E   C   V   L   T   P   S   K   K   L   L   K   R   L   N   E   L   995

2065 GAC GAA AAC CCT ATC AAT GAC AAG GTT AGT TTG TTA GCA CGC GAT AGT TTT 2124
 996  D   E   N   P   I   N   D   K   V   S   L   L   A   R   D   S   F   515

2125 AAT GCA GAA AAA ATG CGC TCC TTT TTA GCC CCC TTG AAC GAG CGG GTT TTA 2184
 516  N   A   E   K   M   R   S   F   L   A   P   L   N   E   R   V   L   535

2185 GAG CAG ATT AAA ATT GAA TGC AAA TAT AAT ATT GAA AAG CAA CAC GAA AAT ATC 2244
 536  E   Q   I   K   I   E   C   K   Y   N   I   E   K   Q   H   E   N   I   555

2245 GCT AAA ATG GAT AGC ATG CTC AAA GTT TCT ATC CCT AAA GGA TTC CGC AAA GGC ATT 2304
 556  A   K   M   D   S   M   L   K   V   S   I   P   K   G   F   R   K   G   I   575

2305 CCA GGC TTA AGC TCA GAA AAA TTA GAA GCG AAT TTA GAC GTT TTG CAT TTA TAC ATC TTT 2369
 576  P   G   L   S   S   E   K   L   E   A   N   L   D   V   L   H   L   Y   I   F   595

2365 GAA GCC TCA GAA ATC AGC GGG ATC ACT CCA GCG AAT TTA GAC GTT TTG CAT TTA TAC ATC 2424
 596  E   A   S   E   I   S   G   I   T   P   A   N   L   D   V   L   H   L   Y   I   615
                                       S.D.
2425 CAT TTG CGA AAA AAC TCT TAA aggattttta ATG AAC GCT TTA GAA ATC ACC CAA AAG CTC 2485
 616  H   L   R   K   N   S   *                M   N   A   L   E   I   T   Q   K   L   10
```

FIG.2 Cont.3

Figure 2:
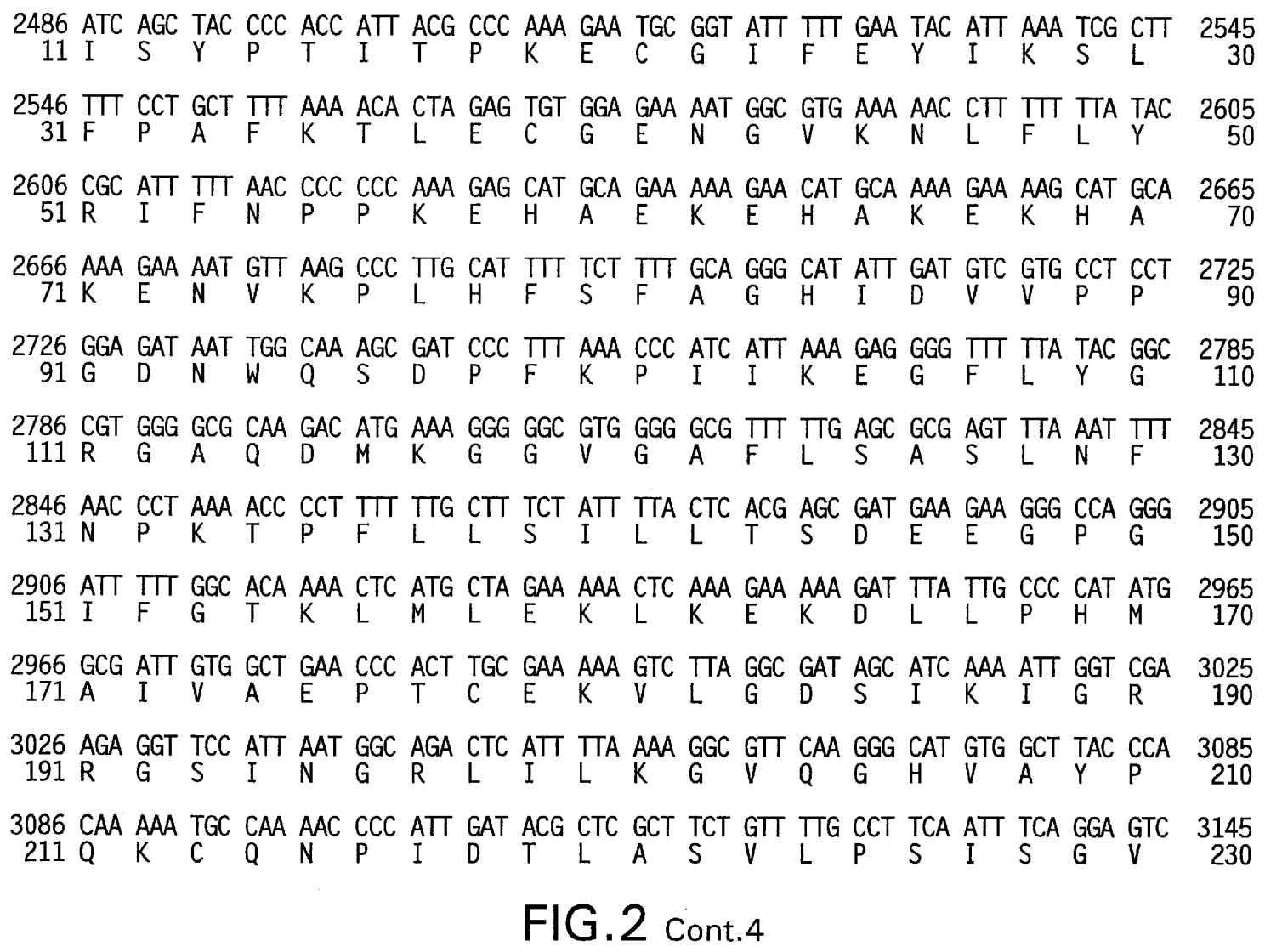

| | | | | | | | | | | |
|---|---|---|---|---|---|---|---|---|---|---|
| 2486 ATC<br>11 I | AGC<br>S | TAC<br>Y | CCC<br>P | ACC<br>T | ATT<br>I | ACG<br>T | CCC<br>P | AAA<br>K | GAA<br>E | TGC<br>C | GGT<br>G | ATT<br>I | TTT<br>F | GAA<br>E | TAC<br>Y | ATT<br>I | AAA<br>K | TCG<br>S | CTT<br>L | 2545<br>30 |

(table is not preserved — figure follows)

FIG. 2 Cont. 4

```
3146 CAT TTA GAC GAT GGC GAT GAA TAT TTT GAC CCT TCA AAA TTG GTT GTC ACC AAC TTG CAT 3205
231  H   L   D   D   G   D   E   Y   F   D   P   S   K   L   V   V   T   N   L   H   250

3206 GCA GGG TTA GGG GCT AAT AAT GTG ACT CCA GGG AGC GTA GAA ATT ACC TTT AAT GCG CGC 3265
251  A   G   L   G   A   N   N   V   T   P   G   S   V   E   I   T   F   N   A   R   270

3266 CAT TCT TTA AAA ACC ACC AAA GAG AGT TTG AAA GAA TAT TTA GAA AAA GTT TTA AAA GAT 3325
271  H   S   L   K   T   T   K   E   S   L   K   E   Y   L   E   K   V   L   K   D   290

3326 TTG CCT CAC ACT TTA GAA TTA GAG TCA AGC AGT TCG CCT TTC ATC ACG GCT TCT CAT TCA 3385
291  L   P   H   T   L   E   L   E   S   S   S   S   P   F   I   T   A   S   H   S   310

3386 AAG CTT ACC AGC GTT TTA AAA GAA AAT ATT TTA AAA ACA TGC CGC ACC ACC CCC CTT TTA 3445
311  K   L   T   S   V   L   K   E   N   I   L   K   T   C   R   T   T   P   L   L   330

3446 AAC ACC AAA GGC GGC ACG AGC GAT GCG CGA TTT TTT AGC GCT CAT GGT ATA GAA GTG GTG 3505
331  N   T   K   G   G   T   S   D   A   R   F   F   S   A   H   G   I   E   V   V   350

3506 GAG TTT GGC GTT ATT AAT GAC AGG ATC CAT GCC ATT GAT GAA AGG GTG AGC TTG AAA GAA 3565
351  E   F   G   V   I   N   D   R   I   H   A   I   D   E   R   V   S   L   K   E   370

3566 TTA GAG CTT TTA GAA AAA GTG TTT TTG GGG GTT TTA GAG GGC TTG AGT GAG GGC AAA TAA aata 3626
371  L   E   L   L   E   K   V   F   L   G   V   L   E   G   L   S   E   A   *         389

3627 aataacattaagtaaggcttatcaatatttgattacaattataaaggttacatttttaataggagatatacc ATG 3705
                                                                S.D.              M    1

3706 CTA GGA AGC GTT AAA AAA ACC TTT TTT TGG GTC TTG TGT TTG GGC GCG TTG TGT TTA AGA 3765
  2  L   G   S   V   K   K   T   F   F   W   V   L   C   L   G   A   L   C   L   R   21

3766 GGG TTA ATG GCA GAG GAG CCA GAC GCT AAA GAG CTT GTT AAT TTA GGC ATA GAG AGC AAG 3825
 22  G   L   M   A   E   E   P   D   A   K   E   L   V   N   L   G   I   E   S   K   41
```

FIG. 2 Cont. 5

| | | | | | | | | | | | | | | | | | | | |
|---|---|---|---|---|---|---|---|---|---|---|---|---|---|---|---|---|---|---|---|
|3826|AAG|CAA|GAT|TTC|GCT|CAA|GCT|AAA|ACG|CAT|TTT|GAA|AAA|GCT|TGT|GAG|TTA|AAA|AAT|GGC|3885|
|42|K|Q|D|F|A|Q|A|K|T|H|F|E|K|A|C|E|L|K|N|G|61|
|3886|TTT|GGG|TGT|GTT|TTT|TTA|GGG|GCG|TTC|TAT|GAA|GAA|GGA|GTG|GGA|AAA|GAC|TTG|3945|
|62|F|G|C|V|F|L|G|A|F|Y|E|E|G|V|G|K|D|L|81|
|3946|AAA|GCC|ATC|CAG|TTT|TAC|TAT|AAA|AGT|TGT|GAA|TTA|AAT|GAT|GGT|TAT|GGG|TGC|AAC|4005|
|82|K|A|I|Q|F|Y|Y|K|S|C|E|L|N|D|G|Y|G|C|N|101|
|4006|CTG|CTA|GGA|AAT|TTA|TAC|TAT|AAC|GGA|CAA|GGC|GTA|TCT|AAA|GAC|GCT|AAA|AAA|GCC|TCA|4065|
|102|L|L|G|N|L|Y|Y|N|G|Q|G|V|S|K|D|A|K|K|A|S|121|
|4066|CAA|TAC|TAC|TCT|AAA|GCT|TGC|GAC|CAT|GCT|GAA|GGG|TGT|ATG|GTA|TTA|GGA|AGC|4125|
|122|Q|Y|Y|S|K|A|C|D|H|A|E|G|C|M|V|L|G|S|141|
|4126|TTA|CAC|CAT|TAT|GGC|GTA|ACG|GGC|CCT|AAG|GAT|TTA|AGA|AAG|GCT|CTT|GAT|TTG|TAT|GAA|4185|
|142|L|H|H|Y|G|V|T|G|P|K|D|L|R|K|A|L|D|L|Y|E|161|
|4186|AAA|GCT|TGC|GAT|TTT|AAA|GAG|GTT|ATC|AGC|CCA|GGG|TGT|ATT|AAT|GCA|GGA|TAT|ATA|TAT|4245|
|162|K|A|C|D|F|K|E|V|I|S|P|G|C|I|N|A|G|Y|I|Y|181|
|4246|ACA|AAG|AAT|TTA|AAA|GAC|AGC|CCA|ATC|GTT|CGT|TAT|TCT|CAA|TAC|AAC|GCT|GAG|TTG|AAC|4305|
|182|T|K|N|L|K|D|S|P|I|V|R|Y|S|Q|Y|N|A|E|L|N|201|
|4306|AGG|GGG|TGT|TAT|AAT|TTA|GGG|GTT|ATG|CAA|AAA|AAA|GGT|TGC|AAA|GCT|CAA|GGC|ACA|GCA|4365|
|202|R|G|C|Y|N|L|G|V|M|Q|K|K|G|C|K|A|Q|G|T|A|221|
|4366|AAG|CAA|GCG|GTA|GAA|AAC|TTT|AAG|GAG|GTT|TGC|AAA|TCA|GCC|GTT|AAA|GAA|GCA|TGC|GAC|4425|
|222|K|Q|A|V|E|N|F|K|E|V|C|K|S|A|V|K|E|A|C|D|241|
|4426|GCT|CTC|AAG|GAA|TTG|AAA|ATA|GAA|CTT|TAG|tttcaataagttaagccaaacgccgtgtttagctggctt|4495|
|242|A|L|K|E|L|K|I|E|L|*| |251|

FIG. 2 Cont.6

```
4496 ctacgcttttaatatcttaatgaaagcataaacctacaaactaatcttttaatcataataagggttttatatcgcacc 4575

4576 cattcattgccgttttagattggcgcttgaaggtttaaagcaagtttgttcaacccttaaaaagggttttaaccc     4654

4655 cta caa cgc ttt caa tag cac gct att tag gcg ttc ggt aaa act ttt agc gtc ttt taa 4714
     gat gtt gcg aaa gtt atc gtg cga taa atc cgc aag cca ttt tga aaa tcg cag aaa att
      *   L   A   K   L   L   V   S   N   L   R   E   T   F   S   K   A   D   K   L 4715 agc ccc ttt atc ttc taa aag ctt cgc ccc atc ata aag caa cca gat aaa agc gtt caa ctg 4774
     tcg ggg aaa aag att ttc gaa gcg tag ggg tag ttt gtt ggt cta ttt tcg caa gtt gac
      A   G   K   E   L   L   K   A   G   D   Y   L   L   W   I   F   A   N   L   Q 4775 ctc ttt atc ttc gca ttt taa gag ttt ttg gaa aat cgc atg gtt agg gtt taa ttc tag 4834
     gag aaa tag cgt aaa att ctc aaa act cct tta gcg tac caa att aag atc
      E   K   D   E   C   K   L   K   F   I   A   H   N   P   N   L   E   L 4835 cgt ttt ctt gct ttc agg cac gct ttg acc cat agt gag cac cgc aaa att agc cat cat cgc 4894
     gca aaa cga cga aag tcc gtg cga aac tgg gta ctc tca act gtg gcg ctc gag atg gcg
      T   K   S   E   P   V   S   Q   M   R   L   H   S   T   L   H   A   M   M   A 4895 att ttg gtc atc gcc tat taa agc cac cgc tga agt gag atg act gga aag ctc tac gcc 4954
     taa aac cag tag cgg ata att tcg gtg gcg act tca ctc tga cct ttc gag atg cgg
      N   Q   D   D   G   I   L   A   V   A   S   T   L   H   S   L   E   V   G 4955 ttt aat ctc atc ttt aag att ttc aaa cgc ttt cat taa atc ttt aaa ctg atc ttt    5014
     aaa tta gag tag ttc taa aag ttt gcg aaa gta att tag gac tag aaa
      K   I   E   D   L   N   E   F   A   K   M   L   D   K   F   Q   D   K 5015 tat ctc atc aag gat ttc caa acc aag ggt taa                                    5050
     ata gag tag ttc cta aag gtt tgg ttc cca att
      I   E   D   L   I   E   L   G   L   T
```

FIG.2 Cont.7

```
H.inf.   1 MFYTETYDVIVIGGGHAGTEAALAPARMGFKTLLLTHNVDTLGQMSCNPA  50
           ...|::|||||||||.||.| :|:|| :. .|: :|||:|  |||||
H.pyl.   1 ..MVKESDILVIGGGHAGIEASLIAAKMGARVHLITMLIDTIGLASCNPA  48
           ...|::::|||||||||.||.: ||:||... |:| |||:|  |||||
E.coli   1 MFYPDPFDVIIIGGGHAGTEAAMAAARMGQQTLLLTHNIDTLGQMSCNPA  50

51 IGGIGKGHLVKEVDAMGGLMAHAADKAGIQFRTLNSSKGPAVRATRAQSD 100
           |||:|||||.||||.:|| |:  .|..|:|:|.||.|||||||:|||| |
        49 IGGLGKGHLTKEVDVLGGAMGIITDHSGLQYRVLNASKGPAVRGTRAQID  98
           |||:|||||.||||.||| |: .|:.|:|:|:|||||||||||:|||| |
        51 IGGIGKGHLVKEVDALGGLMAKAIDQAGIQFRILNASKGPAVRATRAQAD 100

101 RVLYRQAVRTALENQPNLDIFQQEATDILIEQDRVTGVSTKMGLTFRAKS 150
           . ||  .|. : | |||.: |:  ...:::|.| |.||.|.:. |:|||.
        99 MDTYRIFARNLVLNTPNLSVSQEMTESLILENDEVVGVTTNINNTYRAKK 148
           . ||  .|. : | ||| : |: .|.||:||| |||..|.:. .:|||
       101 RVLYRQAVRTALENQPNLMIFQQAVEDLIVENDRVVGAVTQMGLKFRAKA 150

151 VILTAGTFLAGKIHIGLENYEGGRAGDSASVNLSHRLRDLGLRVDRLKTG 200
           ||:|.||||   |:|||  .. :.|| |:.||   .|.  .||:||::|:|||||
       149 VIITTGTFLKGVVHIGEHQNQNGRFGENASNSLALNLRELGFKVERLKTG 198
           |::|.||||.| :||| .. .|| |: :| .|. .||||.:::|:|||||
       151 VVLTVGTFLDGKIHIGLDNYSGGRAGDPPSIPLSRRLRELPLRVGRLKTG 200

201 TPPRIDARTINFDILAKQHGDEVLPVFSFMGSVDDHPQQIPCYITHTNEQ 250
           |.||:.:..|:|: |..: ||. | ||:... | :| |:.|:||.||.
       199 TCPRVAGNSIDFEGLEEHFGDANPPYFSYKTKDF.NPTQLSCFITYTNPI 247
           |.||:.:..|||..|.::  ||. | ||:.... :| |:.|:||.||.
       201 TPPRIDARTIDFSVLAQQHGDNPMPVFSFMGNASQHPQQVPCYITHTNEK 250

251 THEVIRNNLDRSPMYTGVIEGIGPRYCPSIEDKVMRFADRNSHQIYLEPE 300
           ||::||:|:.|.|:::.| |||||||||||||||||: ||.::.:||::|||:
       248 THQIIRDNFHRAPLFSGQIEGIGPRYCPSIEDKINRFSEKERHQLFLEPQ 297
           ||::||.|.|:.|:::.| |||||:||||||||||||: ||.::.:||:|||||
       251 THDVIRSNLDRSPMYAGVIEGVGPRYCPSIEDKVMRFADRNQHQIFLEPE 300

301 GLTSNEVYPNGISTSLPFDVQMGIVNSMKGLENARIVKPGYAIEYDYFDP 350
           .: .|| | ||:|||||||:||| :::|:|||||| |.:  ||||||||:::|
       298 TIHKNEYYINGLSTSLPLDVQEKVIHSIKGLENALITRYGYAIEYDFIQP 347
           .: .||.| ||:|||||||:||| .::::|..|:|||  |.| ||||||||::|
       301 GLTSNEIYPNGISTSLPFDVQMQIVRSMQGMENAKIVRPGYAIEYDFFDP 350

351 RDLKPTLETKSISGLFFAGQINGTTGYEEAAAQGLLAGINAGLYVQEKDA 400
           :|...||||.|.||::|||||||||||||||||||.|||:||||||.| :.:..:
       348 TELTHALETKKIKGLYLAGQINGTTGYEEAADQGLMAGINAVLALKNQAP 397
           :|...||.| |.|::|||||||||||||||||||||.|||:||:||. ....
       351 RDLKPTLESKFIQGLFFAGQINGTTGYEEAAAQGLLAGLNAARLSADKEG 400
```

FIG.3A

```
401 WYPRRDQSYTGVLVDDLCTLGTKEPYRVFTSRAEYRLLLREDNADIRLTP 450
    :..  :|:::.|.|||:|||.|  ||.||||:|||||||||||||.  :||..
398 FILKRNEAYIGVLIDDLVTKGTNEPYRMFTSRAEYRLLLREDNTLFRLGE 447
    :    |.:||:|||:|||.|  ||.||||||||||||:|||||.  :||.|
401 WAPARSQAYLGVLVDDLCTLGTKEPYRMFTSRAEYRLMLREDNADLRLTE 450

451 IAHELGLIDEARWARFNQKMENIEQERQRLRSIWLHPRSEYLEEANKVLG 500
     |.  |||:::.  :    :.....::|:::  .||:..  |   |....|.    |.:  :
448 HAYRLGLMEQDFYKELKKDKQEIQDNLKRLKECVLTPSKKLLKRLNELDE 497
    :    |||::::  :    :...  ::|:  :  .|||..  :|||    .         :|.    .
451 IGRELGLVDDERWARFNEKLENIERERQRLKSTWVTPSAEAAAEVNAHLT 500

501 SPLVREASGEDLLRRPEMTYDILTSLTPYKPAMEDKEAVEQVEIAIKYQG 550
    .|:    ...|    .||    |...:  .  :    |:  .:  :::::::    .:||:.|..||.
498 NPINDKVNGVSLLARDSFNAEKMRSFFSFLAPL.NERVLEQIKIECKYNI 546
    .|:..   ...|    .||    |..:.  ||:    .:    .|    ::|  :|..    ||:.|:.||:
501 APLSREASGEDLL.RPEMTYEKLTTLTPFAPALTDEQAAEQVEIQVKYEG 549

551 YIEHQQNFDYSKVS................GLSNEVRAKLEQHRPVSIGQ 583
    |||.|         |                                  |||         |||||   || |:
547 YIEKQHENIAKMDSMLKVSIPKGFVFKGIPGLSLEAVEKLEKFRPKSLFE 596
    ||.:|:::|.|     .    ..  :|  .:  ::.:.|||  |    ||        |    :  :
550 YIARQQDEIEKQLRNENTLLPATLDYRQVSGLSNEVIAKLNDHKPASIGQ 599

584 ASRISGITPAAISI..ILVNLKKQGMLKRGE 613
    ||  |||||||.:.:     :.::|:|.:
597 ASEISGITPANLDVLHLYIHLRKNS...... 621
    ||  |||:|||.:.:|  ::      |:|.:
600 ASRISGVTPAAISILLVW..LKKQGMLRR   626
```

FIG.3A Cont.

```
H.inf.   1 MKEKVVSLAQDLIRRPSISPNDEGCQQIIAERLEKL........G.FQIEW  42
           ..:.:.|.||. |.|.|.: |. :.| . :.  :   : .:.
H.pyl.   1 ..MNALEITQKLISYPTITPKECGIFEYIKSLFPAFK.TLECGE.NGVKN  46
           .:|:||.||. |.:.|..:.|. ..:  ..:.|:  |:|   : .:..|
E.coli   1 MSCPVIELTQQLIRRPSLSPDDAGCQALLIERLQAIGFTVERMDFADTQN  50

43 MPFNDTLNLWAKHGTSEPV.............IAFAGHTDVVPTGDENQW  79
           : :  ..:|   .|:..|..       :.||||.||||.||: |
        47 LFLYRIFNPPKEHAEKEHAKEKHAKENVKPLHFSFAGHIDVVPPGDN..W  94
           :: :|       :::|.           :.||||.||||||. |
        51 FWAWR......GQGET..............LAFAGHTDVVPPGDADRW   78

80 SSPPFSAEIIDGMLYGRGAADMKGSLAAMIVAAEEYVKANPNHKGTIALL 129
           |.||.: | :|:|||||.||||::::|:: |.  ::  ||. . :.:|
        95 QSDPFKPIIKEGFLYGRGAQDMKGGVGAFLSASLNF...NPKTPFLLSIL 141
           ..||.|.|::|:|:||||.|||||::::| ..| .:|.  |:.| |
        79 INPPFEPTIRDGMLFGRGAADMKGSLAAMVVAAERFVAQHPNHTGRLAFL 128

130 ITSDEEATAKDGTIHVVETLMARDEKITYCMVGEPSSAKNLGDVVKNGRR 179
           :||||:.: || ::|.|...|    .:|:||..:| ||| :| |||
       142 LTSDEEGPGIFGTKLMLEKLKEKDLLPHMAIVAEPTCEKVLGDSIKIGRR 191
           :||||:.: || ::| |...:    ..:|:||.: .|:|| :| |||
       129 ITSDEEASAHNGTVKVVEALMARNERLDYCLVGEPSSIEVVGDVVKNGRR 178

180 GSITGNLYIQGIQGHVAYPHLAENPIHKAALFLQELTTYQWDKGNEFFPP 229
           |||.|.|.::.|:||||||| ..:|||.. | .|...... ::|.|:|.|
       192 GSINGRLILKGVQGHVAYPQKCQNPIDTLASVLPSISGVHLDDGDEYFDP 241
           ||:...|..:.|||||||||| ..:||:. |..| .: :::|:|:|:|.:
       179 GSLTCNLTIHGVQGHVAYPHLADNPVHRAAPFLNELVAIEWDQGNEFFPA 228

230 TSLQIANIHAGTGSNNVIPAELYIQFNLRYCTEVTDEIIKQKVAEMLEKH 279
           ..| :.:|||  |.|||.|:: ||| |.: ..|.| :|. : ...:|.
       242 SKLVVTNLHAGLGANNVTPGSVEITFNARHSLKTTKESLKEYLEKVLK.. 289
           ..: :.|::|| |.|||.||.: ||  |.| | | . |.| :|. : :|.
       229 TSMQIANIQAGTGSNNVIPGELFVQFNFRFSTELTDEMIKAQVLALLEKH 278

280 NLKYRIEWNLSGKPFLT.KPGKLLDSITSAIEETIGITPKAETGGGTSDG 328
           :|.. :|:: |:.||:| ...:|| . :...|  .|. .|| :| |||||:
       290 DLPHTLELESSSSPFITASHSKLTSVLKENILKTCRTTPLLNTKGGTSDA 339
           :|..|::: |: ||:|| ::||...|.: ..|| :| |.||||:
       279 QLRYTVDWWLSGQPFLTA.RGKLVDAVVNAVEHYNEIKPQLLTTGGTSDG 327

331 RFIALMGAEVVEFGPLNSTIHKVNEEE................ 355
           ||:. | ||||||.:|. || ::|
       340 RFFSAHGIEVVEFGVINDRIHAIDERVSLKELELLEKVFLGVLEGLSEA 388
           ||:. | :|||:|.:|. ||  |:| |. :|| ::|.|
       328 RFIPRMGAQVVELGPVNATIHKINECVNAADLQLQR......IMEQLVA.. 370
```

DAPE GENE ON *HELICOBACTER PYLORI* AND DAPE⁻ MUTANT STRAINS OF *HELICOBACTER PYLORI*

This application is a national phase of, and claims the benefit of international patent application PCT/US97/24147 filed Dec. 23, 1997, which claims priority from provisional patent application Ser. No. 60/033,824 filed Dec. 23, 1996. The PCT/US97/24147 and 60/033,824 applications are herein incorporated by this reference in their entirety.

This work was supported by NIHR01DK 50837. The government has certain rights in the invention.

BACKGROUND OF THE INVENTION

1. Field of the Invention

The invention pertains to the dapE gene of *Helicobacter pylori* and *H. pylori* dapE⁻ mutants and to methods of using the mutants to express foreign genes and immunize against foreign agents.

2. Background Art

*Helicobacter pylori* are gram negative enteric bacteria that colonize the human gastric mucosa and cause gastritis and peptic ulcer disease (6,11,15) and are implicated in malignant neoplasms of the stomach (5,26,30,37). Thus, there exists a need for a method of treating and preventing *H. pylori* infection.

The present invention meets these needs by providing the dapE gene of *H. pylori* and conditionally lethal mutants of *H. pylori* which can be used to express foreign proteins and to immunize against *H. pylori* infection.

BRIEF DESCRIPTION OF THE FIGURES

FIG. 2 shows the nucleotide and deduced amino acid sequences of the region on the *H. pylori* chromosome including gidA, and dapE, and orf2. SEQ ID NO:7 defines the nucleotide sequence shown in FIG. 2. The sequence of gidA, dapE and orf2, and 579 bp upstream and 595 bp downstream are shown. The 1866 bp gidA commences at nucleotide 580 and ends at nucleotide 2445. The 1167 bp dapE commences at nucleotide 2456 and ends at nucleotide 3622. The 753 bp orf2 commences at nucleotide 3703 and ends at nucleotide 4455. The deduced amino acid sequence is shown beneath the nucleotides. A potential ribosome-binding site (Shine-Dalgarno sequence) and putative promoter elements (−35 and −10 sequences) are indicated. An open reading frame, tentatively called ORF1, which is deduced to be translated in the opposite orientation from gidA begins at nucleotide 483. An open reading frame, tentatively called ORF3, which is deduced to be translated in the opposite orientation from orf2 ends at nucleotide 4655.

FIG. 3A shows alignment of the deduced amino acid sequences of the gidA products in *E. coli* (SEQ ID NO: 27) and *H. influenzae* (SEQ ID NO: 25) and the *H. pylori* homolog (SEQ ID NO: 26). To optimize the alignments, gaps were introduced when necessary. The vertical lines between residues indicate identity whereas two dots represents a conservative substitution.

FIG. 3B shows alignment of the deduced amino acid sequences of the dapE products in *E. coli* (SEQ ID NO: 30) and *H. influenzae* (SEQ ID NO: 28) and the *H. pylori* homolog (SEQ ID NO: 29). To optimize the alignments, gaps were introduced when necessary. The vertical lines between residues indicate identity whereas two dots represents a conservative substitution.

DETAILED DESCRIPTION OF THE INVENTION

Nucleic Acids

Figure 1:
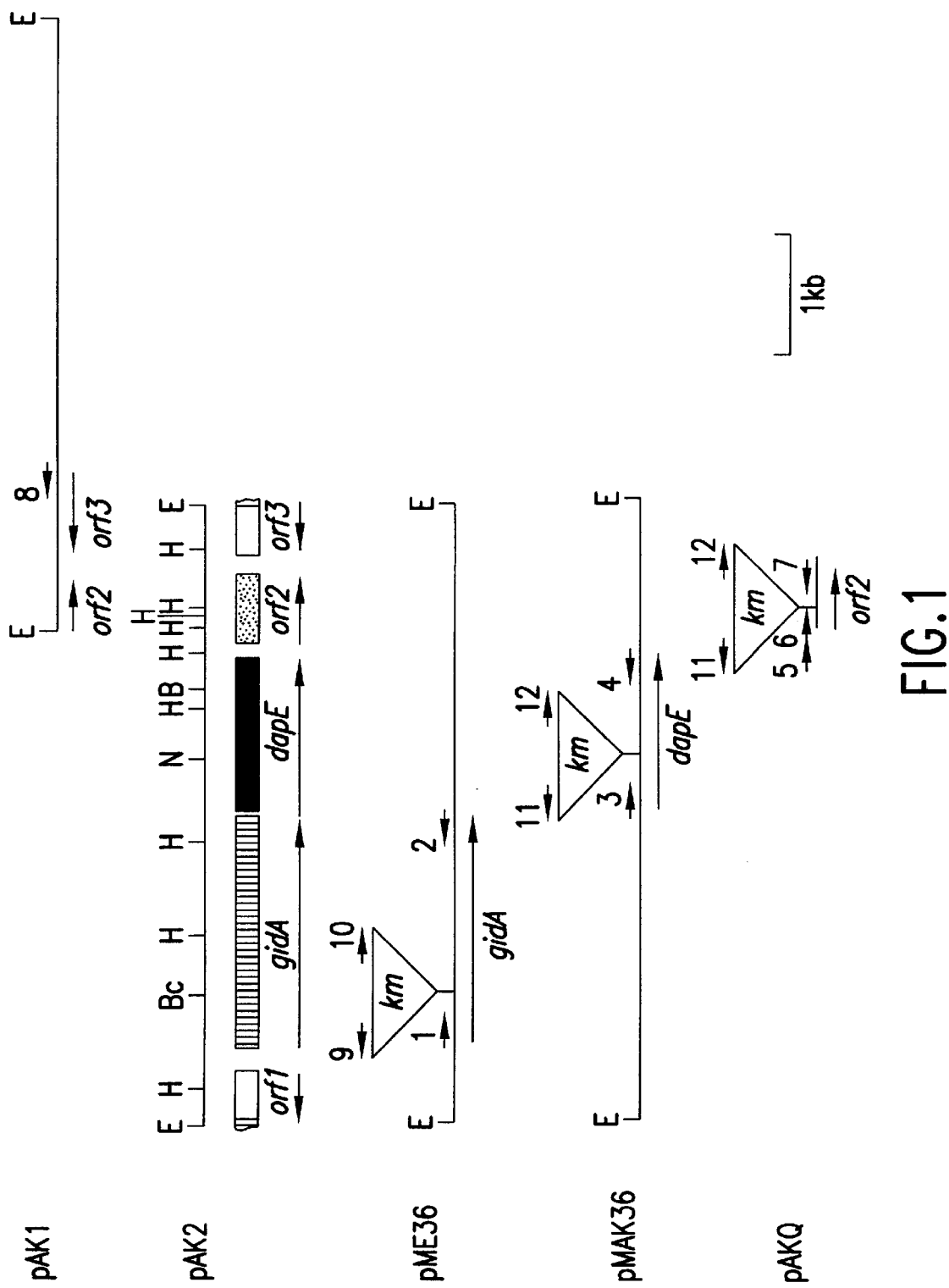
FIG. 1 shows physical maps of recombinant pBluescript plasmids containing gidA, dapE, and orf2. pAK1 contains the 3' region of orf2 plus approximately 4 kb downstream. pAK2 contains a 5 kb EcoRI fragment that includes gidA, dapE, and orf2. Boxes and arrows beneath the plasmids represent the location of the genes and the presumed direction of translation, and km represents a cassette encoding kanamycin-resistance. Arrowheads with numbers represent sites of oligonucleotide primers used in PCR. Restriction endonuclease cleavage sites: Ba (BamHI), Bc (BclI), N (NdeI), E(EcoRI), and H (HindIII).

An isolated dapE gene of *Helicobacter pylori* is provided. "Isolated" means a nucleic acid is separated from at least some of other components of the naturally occurring organism, for example, the cell structural components and/or other genes. The isolation of the nucleic acids can therefore be accomplished by techniques such as cell lysis followed by phenol plus chloroform extraction, followed by ethanol precipitation of the nucleic acids (24). It is not contemplated that the isolated nucleic acids are necessarily totally free of non-nucleic acid components, but that the isolated nucleic acids are isolated to a degree of purification to be useful in a clinical, diagnostic, experimental, or other procedure such as gel electrophoresis, Southern or dot blot hybridization, or PCR. A skilled artisan in the field will readily appreciate that there are a multitude of procedures which may be used to isolate the nucleic acids prior to their use in other procedures. These include, but are not limited to, lysis of the cell followed by gel filtration or anion exchange chromatography, binding DNA to silica in the form of glass beads, filters or diatoms in the presence of high concentration of chaotropic salts, or ethanol precipitation of the nucleic acids.

The nucleic acids of the present invention can include positive and negative strand RNA as well as DNA and is meant to include genomic and subgenomic nucleic acids found in the naturally occurring organism. The nucleic acids contemplated by the present invention include double stranded and single stranded DNA of the genome, complementary positive stranded cRNA and mRNA, and complementary cDNA produced therefrom and any nucleic acid which can selectively or specifically hybridize to the isolated nucleic acids provided herein.

The dapE gene can consist of the nucleotide sequence defined in SEQ ID NO:3. Other examples of the dapE gene of *H. pylori* can be found in any *H. pylori* isolate. Although there may be small differences (e.g., point mutations) among the dapE genes of *H. pylori* strains, these differences, if any, do not prevent the isolation and sequencing or other uses of this gene from other *H. pylori* strains. Thus, primers from the present dapE sequence can be used to amplify dapE from any sample in which it occurs, and oligonucleotide segments of the exemplified dapE gene can be used to probe a sample for the presence of the *H. pylori* dapE or, more generally, *H. pylori*. It may be preferable to use slightly longer primers than the standard primers of 17 nucleotides, for example, primers of approximately 25 nucleotides.

The dapE gene can be distinguished from other nucleic acids, because of its conserved genomic location. Particularly, dapE is flanked upstream by gidA and downstream by orf2. This conserved location also makes obtaining dapE from other *H. pylori* strains routine and predictable. For example, primers that hybridize with the highly conserved gidA and orf2 can be used to amplify dapE from any sample in which it occurs. Similarly, a primer that hybridizes with one or the other of the highly conserved gidA and orf2 can be paired with a primer from the exemplified dapE to amplify dapE (or a segment of it) from any sample in which it occurs. Additionally, since the position of this gene in the *H. pylori* genome is known, it can be mutated in any strain, according to the methods taught herein.

DapE-encoding nucleic acids can be isolated from *H. pylori*) using any of the routine techniques. For example, a genomic DNA or cDNA library can be constructed and screened for the presence of the nucleic acid of interest using one of the present dapE nucleic acids as a probe. Methods of constructing and screening such libraries are well known in the art and kits for performing the construction and screening steps are commercially available (for example, Stratagene Cloning Systems, La Jolla, Calif.). Furthermore, genomic DNA can be isolated from an *H. pylori* strain and screened using one of the present dapE nucleic acids as a probe. Once isolated, the dapE nucleic acid can be directly cloned into an appropriate vector, or if necessary, be modified to facilitate the subsequent cloning steps. Such modification steps are routine, an example of which is the addition of oligonucleotide linkers which contain restriction sites to the termini of the nucleic acid. General methods are set forth in Sambrook et al. (24).

A *H. pylori*-specific nucleic acid fragment of the dapE gene is provided. For example, the fragment can consist of the nucleotide sequence of the 1.1 kb dapE-specific fragment, further described in the Examples. Other examples can be obtained routinely using the methods taught herein and in the art.

A nucleic acid that encodes a naturally occurring DapE protein of *Helicobacter pylori* and hybridizes with the nucleic acid of SEQ ID NO:3 under the stringency conditions of about 16 hrs at about 65° C., about 5×SSC, about 0.1% SDS, about 2×Denhardt's solution, about 150 µg/ml salmon sperm DNA with washing at about 65° C., 30 min, 2×, in about 0.1×SSPE/0.1% SDS is provided. Alternative hybridization conditions include 68° C. for about 16 hours in buffer containing about 6×SSC, 0.5% sodium dodecyl sulfate, about 5×Denhardt's solution and about 100 µg salmon sperm DNA, with washing at about 60° C. in about 0.5×SSC (Tummuru, M. K. R., T. Cover, and M. J. Blaser (24).

A nucleic acid probe that hybridizes with the nucleic acid of SEQ ID NO:3 under either of the above described stringency conditions can be used to identify dapE in other strains of *H. pylori*.

A nucleic acid primer that hybridizes with the nucleic acid of SEQ ID NO:3 under the polymerase chain reaction conditions of 35 cycles of 94° C. for 1 min, 50° C. for 2 min, and 72° C. for 2 min, with a terminal extension at 72° C. for min. These conditions can be used with the relevant primers to identify dapE, including interstrain variants. Examples of these primers are described in the Examples.

The selectively hybridizing nucleic acids of the invention can have at least 70%, 80%, 85%, 90%, 95%, 97%, 98% and 99% complementarity with the segment and strand of the sequence to which it hybridizes. The nucleic acids can be at least 15, 18, 20, 25, 50, 100, 150, 200, 300, 500, 750, 1000, 2000, 3000 or 4000 nucleotides in length. Thus, the nucleic acid can be an alternative coding sequence for the *H. pylori* dapE, or can be used as a probe or primer for detecting the presence *H. pylori*. If used as primers, the invention provides compositions including at least two nucleic acids which selectively hybridize with different regions so as to amplify a desired region. Depending on the length of the probe or primer, it can range between 70% complementary bases and full complementarity with the segment to which it hybridizes. For example, for the purpose of diagnosing the presence of *H. pylori*, the degree of complementarity between the hybridizing nucleic acid (probe or primer) and the sequence to which it hybridizes (*H. pylori* DNA from a sample) should be at least enough to exclude hybridization with a nucleic acid from related bacterium. Thus, a nucleic acid that selectively hybridizes with a *H. pylori* DapE coding sequence will not selectively hybridize under stringent conditions with a nucleic acid for a DapE of another species, and vice versa. The degree of complementarity required to distinguish selectively hybridizing from nonselectively hybridizing nucleic acids under stringent conditions can be clearly determined for each nucleic acid. It should also be clear that a selectively hybridizing nucleic acid will not hybridize with nucleic acids encoding unrelated proteins.

Nucleic acids of the gidA gene and ORF2 of *H. pylori* are provided. Examples of these nucleic acids can be found in SEQ ID NO:1 and SEQ ID NO:5, respectively. Having provided these nucleic acids, hybridizing nucleic acids in accord with the description of hybridizing nucleic acids of dapE are also provided.

The nucleic acids of the invention (dapE, gidA and ORF2, and their fragments) can also be in a composition such as a genetic construct, which includes other nucleic acids such as origins of replication, promoters, other protein coding sequences, etc. The composition can also, or alternatively, contain compounds, such as non-nucleic acid marker molecules attached to the nucleic acids.

Vectors

The DapE-encoding nucleic acid and selectively hybridizing nucleic acids of the invention can be in a vector suitable for expressing the nucleic acid. The nucleic acid in a vector can be in a host suitable for expressing the nucleic acid.

A plasmid comprising a nucleic acid encoding a functional DapE protein of *H. pylori* is provided. The plasmid can further comprise a nucleic acid encoding a non-*H. pylori* (foreign) protein. The foreign protein encoded can be immunogenic, antigenic, or enzymatic proteins of bacteria, virus, fungus or parasite. For example the protein can be from Salmonella (*Salmonella enteritidis*), Shigella species, Yersinia, enterotoxigenic and enterohemorrhagic *E. coli, Mycobacterium tuberculosis, Streptococcus pyogenes, Bordatella pertussis, Bacillus anthracis, P. falciparum*, human immunodeficiency virus, respiratory syncytial virus, influenza virus, *histoplasma capsulatum* or other infectious organisms.

Other foreign proteins include sperm antigens for use to immunize against sperm as a form of birth control. Also contemplated are immunomodulating proteins to treat against inflammatory diseases and cytotoxic proteins to treat against malignancies. Likewise, the foreign protein need not be an antigen, but can instead be protein of the host. In this embodiment the *H. pylori* mutant strain is used to express a host protein in vivo to provide or augment an activity of the host protein. Thus, the *H. pylori* dapE⁻ mutant can include an insulin gene for use in a method of delivering insulin to diabetics or it can include a gene for TNF for modulating or augmenting the host response to stress. In each case the amount of DAP provided to the host can be used to control the amount of the protein that is expressed. As noted elsewhere in the application, the *H. pylori* dapE⁻ strain can also have other introduced attenuating mutations or it can be a naturally occurring vacuolating toxin strain.

The plasmids of the present invention can be any of the well know plasmids used in bacteria. For example, the plasmid can include a 1.5 kb HindIII fragment cloned into the polylinker of a pUC vector. One such vector has a kanamycin resistance cassette inserted into this hybrid clone and is called pHP1.

Another shuttle vector that can be used as an example of the type of construct that would be useful, was that described by Schmitt et al. (Mol. Gen. Genetics. 1995. 248:563–472). In the case described, a cryptic *H. pylori* plasmid, pHe1 was ligated with an *E. coli* replicon to prepare an *E. coli-H. pylori* shuttle vector. Schmitt et al. cloned the *H. pylori* recA gene into the shuttle vector to create pDH38 which was introduced into an *H. pylori* strain by natural transformation. This vector was shown to complement the recA deficiency on a parental strain.

Vectors other than plasmids that can be used in *H. pylori* include transducing bacteriophage.

Mutant *H. pylori*

A purified mutant strain of *H. pylori* that does not express a functional DapE protein is provided. The mutant can either not express DapE or express a non-functioning DapE. Such a mutant is also referred to herein as a dapE⁻ mutant. Mutations to the dapE gene on the *H. pylori* chromosome that result in a dapE⁻ mutant can be made by insertion, deletion or internal modification.

In one example, the mutant *H. pylori* strain is obtained by making an insertion substitution mutation in the coding sequence for the DapE as described in the Examples. Since the present invention provides the nucleic acid encoding DapE, other methods of mutating the coding sequence of DapE can be used to obtain other mutant strains as contemplated herein.

One example of the dapE⁻ mutant strain is deposited with the American Type Culture Collection, 12301 Parklawn Drive Rockville, Md. 20852 on Dec. 6, 1996 under accession no. ATCC 55897. This example was made according to one method of making such mutants taught in the Examples.

Additional mutants can be prepared, for example, by inserting a nucleic acid in the dapE gene or deleting a portion of the dapE gene so as to render the gene nonfunctional or protein produced in such low amounts that the organism dies in the absence of DapE supplementation. Furthermore, by providing the nucleotide sequence for the nucleic acid encoding the DapE, the present invention permits the making of specific point mutations having the desired effect. The deletion, insertion or substitution mutations can be made in either the regulatory or coding region to prevent transcription or translation or to render the transcribed and translated product nonfunctional.

One such approach to the construction of a deletion or insertion mutant is via the Donnenberg method (Donnenberg and Kaper Infect. Immun. 4310–4317, 1991). A deletion in dapE is created by deleting a restriction fragment and religating the clone. This mutant is cloned into suicide vector pILL570. The sacB gene of *Bacillus subtilis* is also cloned into the suicide vector to provide a conditionally lethal phenotype. This construct is transformed into *H. pylori* by electroporation, and transformants selected by spectinomycin resistance. The merodiploid strain which contains the suicide vector and the mutated version of the dapE gene are exposed to sucrose to directly select for organisms that have undergone a second recombination, resulting in the loss of the vector. These and other well known methods of making mutations can be applied to the nucleic acids provided herein to obtain other desired mutations. Included are insertional mutagenesis as described in reference 8, as well as linker-scanning mutagenesis (46) and site-directed mutagenesis (47).

Non-isogenic mutants are also within the scope of the invention. For example, a live attenuated *H. pylori* that is also a dapEE⁻ mutant according to the present invention, is provided. A dapE⁻recA⁻ mutant strain is constructed, for example, by insertion mutation of both the dapE and recA genes, according to the methods taught herein for dapE and in U.S. Pat. No. 5,434,253, issued on Jul. 18, 1995 for recA. A dapE⁻recA-cagA- mutant strain is constructed, for example, by insertion mutation of all three genes, according to the methods taught herein, in U.S. Pat. No. 5,434,253 and in U.S. application Ser. No. 08/053,614, which describes the generation of a cagA (referred to therein as tagA) mutant. A dapE⁻recA⁻vacA⁻ mutant strain is constructed, for example, by insertion mutation of all three genes, according to the methods taught herein. A dapE⁻recA⁻cagA⁻vacA⁻ mutant strain is constructed, for example, by insertion mutation of all four genes, according to the methods taught herein and the above cited patents and patent applications. Furthermore, a mutation in dapE combined with any one or more of the above or other mutations can be made. Any of the well known methods of mutating a gene can be used in the present invention to generate *H. pylori* mutant strains. The strains can be tested as provided for immunogenicity, conditional lethality, vacuolating activity, etc.

The dapE⁻ mutant strain can also have in its chromosome a nucleic acid encoding a foreign protein. Briefly, this can be accomplished by inserting SacB in the chromosome as above, then using a suicide vector that has the foreign gene replacing dapE and flanked by gidA and orf2. The suicide vector is then transformed into *H. pylori* using natural transformation conditions such as described in U.S. Pat. No. 5,434,253, and in U.S. application Ser. Nos. 08/053,614, 08/215,928 and 08/200,232. After transformation the *H. pylori* is then grown on sucrose-containing plates. This selects for replacement of the sacB insert by the foreign gene.

The foreign protein encoded can be as described above.

The dapE⁻ mutant strain can also contain a plasmid comprising a nucleic acid encoding a foreign protein. The foreign protein encoded can be as described above.

The dapE⁻ mutant *H. pylori* can be transformed with, and thus, contain a plasmid comprising a nucleic acid encoding a functional DapE protein. This can be accomplished using natural transformation such as is described in U.S. Pat. No. 5,434,253, and in U.S. application Ser. Nos. 08/053,614, 08/215,928 and 08/200,232. Under the appropriate conditions the dapE⁻ mutant *H. pylori* can express a functioning dapE protein due to trans complementation by the dapE gene on the plasmid. These are the typical growth conditions for *H. pylori*, such as are described in the example.

The mutant *H. pylori* containing a plasmid comprising a nucleic acid encoding a functional DapE protein can include in its chromosome a foreign nucleic acid encoding a foreign protein. A method of inserting a foreign gene in the *H. pylori* chromosome is described above. The mutant *H. pylori* containing a plasmid comprising a nucleic acid encoding a functional DapE protein wherein the plasmid further comprises a nucleic acid encoding a foreign protein is provided.

Having provided the present conditionally lethal dapE⁻ mutant and method of generating such a conditionally lethal mutation in the genome of *H. pylori*, the present invention leads predictably to other conditionally lethal mutations in *H. pylori*. Such mutants include those with mutations in genes essential for cell wall synthesis or particular biochemical pathways for which the product can be used to complement the mutation.

The dapE⁻ mutant strain containing a foreign protein in either its chromosome or in a plasmid can be used as an expression system for expressing the foreign protein.

Foreign Gene Expression Method

The present invention provides methods to deliver foreign antigens via the present dapE⁻ mutant *H. pylori* strain engineered to also contain nucleic acids either in the chromosome or on a plasmid (e.g., an *H. pylori* shuttle plasmid) which express the foreign antigen of interest.

A method is provided for maintaining the expression of a foreign antigen in *Helicobacter pylori*, comprising: a) transforming a mutant *Helicobacter pylori* that does not produce of functioning DapE protein with a plasmid comprising a nucleic acid encoding a functional DapE protein and comprising a nucleic acid encoding the foreign protein; and b) maintaining the mutant *Helicobacter pylori* from step a under conditions that permit expression of the foreign protein. Furthermore, by maintaining the *H. pylori* from step a in medium without added L-DAP, only the *H. pylori* that contain the plasmid will survive.

Screening for *H. pylori* mutants

The present dapE⁻ mutant can be used in a method of screening for and selecting *H. pylori* mutants. Because of the attributes of the dapE⁻ mutant, mutants can be selected without the use of antibiotic resistance. This makes the mutants safer for use in humans, because there is no risk of introducing an organism that is resistant to antibiotics, and thus, not removable by antibiotic treatment. Briefly, dapE is deleted from the chromosome or insertionally mutated and the stain is grown in L-DAP-containing medium. A shuttle vector (plasmid) is constructed that encodes DapE to complement the dapE mutation in the chromosome and encodes a foreign protein. The plasmid is transformed into the dapE⁻ *H. pylori*, which are grown on medium without L-DAP. This selects for maintenance of the plasmid.

It should be noted that in the methods and compositions described, the foreign antigen gene can either be in the chromosome replacing dapE or elsewhere in the chromosome. The foreign gene can be on the plasmid that encodes DapE, so that dapE⁻ strains can be used as hosts for any number (multiple copies) or type (cocktail) of gene that may be on any number of plasmids. These strains are expected to survive well since functional DapE is provided. They can be attenuated elsewhere, for example in recA or in vacA so that they are less toxic.

Immunization Methods

An immunogenic amount of the dapE⁻ mutant *H. pylori* in a pharmaceutically acceptable carrier can be used as a vaccine.

A method is provided for immunizing a subject against infection with *Helicobacter pylori*, comprising: a) administering to the subject the dapE⁻ mutant strain of *H. pylori*; b) supplementing the subject's diet with diaminopimelic acid (DAP) in the form of L-DAP or meso DAP (a mixture of L-DAP and D-DAP) to maintain the mutant strain in the subject at least long enough for the subject to mount an immune response to the strain; and c) ceasing the supplementation of the subject's diet with diaminopimelic acid to kill the mutant strain in the immunized subject. The immunization methods described herein comprise administering to the subject an immunogenic amount of mutant *H. pylori* in a pharmaceutically acceptable carrier for the mutant. The length of time to which the subject is exposed to the mutant strain, i.e., the length of time L-DAP supplementation is provided, will typically be from a few days (2 or 3) up to a few weeks (2 or 3). The exact time course may vary from individual to individual and can be verified by tests for the presence of an immune response such as indicated by the presence of antibodies against the *H. pylori* in a tissue sample (e.g., gastric juice, blood, plasma, urine and saliva) from the subject.

A method of immunizing a subject against bacterial infection is provided, comprising: a) administering to the subject the dapE⁻ mutant strain having in its chromosome a nucleic acid encoding a foreign protein (e.g., an immunogen of the bacterium); b) supplementing the subject's diet with L-DAP to maintain the mutant strain in the subject at least long enough for the subject to mount an immune response to the strain; and c) ceasing the supplementation of the subject's diet with diaminopimelic acid to kill the mutant strain in the immunized subject. The immunization methods described herein comprise administering to the subject an immunogenic amount of mutant *H. pylori* in a pharmaceutically acceptable carrier for the mutant. The length of time to which the subject is exposed to the mutant strain is as described above. The exact time course will vary from individual to individual and can be verified by tests for the presence of an immune response such as is measured by assays for antibodies against the foreign protein in a tissue sample (e.g., gastric juice, blood, plasma, urine and saliva) from the subject.

A method of immunizing a subject against a bacterial infection, comprising: a) administering to the subject the dapE⁻ mutant strain containing a plasmid comprising a nucleic acid encoding a foreign protein; b) supplementing the subject's diet with diaminopimelic acid to maintain the mutant strain in the subject at least long enough for the subject to mount an immune response to the strain; and c) ceasing the supplementation of the subject's diet with diaminopimelic acid to kill the mutant strain in the immunized subject.

In the above methods wherein the foreign antigen encoding gene is on the dapE-containing plasmid, the host strain can be attenuated in other genes (e.g., recA, vacA, etc.)

The present immunization methods are useful in immunizing against infection with bacteria, fungi, protozoa and viruses. Thus, the foreign protein encoded can be an antigen (immunogen) of the bacterium, virus, fungus or protozoan against which immunization is being made. The foreign protein encoded can be immunogenic, antigenic, or enzymatic proteins of Salmonella (*Salmonella enteritidis*), Shigella, Yersinia, enterotoxigenic and enterohemorrhagic *E. coli*, *M. tuberculosis*, *Streptococcus pyogenes*, *P. falciparum*, human immunodeficiency virus, respiratory syncytial virus, influenza virus or other infectious organisms. Other foreign proteins include sperm antigens for use to immunize against sperm as a form of birth control or immunomodulating proteins or cytotoxic proteins as described above. The immunization methods for these microorganisms also comprise administering to the subject an immunogenic amount of mutant *H. pylori* containing the gene for a foreign immunogen in a pharmaceutically acceptable carrier for the mutant. The length of time to which the subject is exposed to the mutant strain, i.e., the length of time L-DAP supplementation is provided, will typically be from a few days (2 or 3) up to a few weeks (2 or 3). The exact time course may vary from individual to individual and can be verified by tests for the presence an of immune response (e.g., by the presence of antibodies) against the foreign protein in a tissue sample (gastric juice, blood, plasma, urine and saliva) from the subject. Clearly, if the subject produces antibodies against the microorganism, it is understood that the antibodies are against the recombinant protein produced by the altered *H. pylori* strain.

Determining Immunogenicity and Immunogenic Amounts

The isolated mutant strains of the invention can be tested to determine their immunogenicity. Briefly, various concentrations of a putative immunogen are prepared and administered to an animal and the immunological response (e.g., the production of antibodies or cell mediated immunity) of an animal to each concentration is determined. The amounts of antigen administered depend on the subject, e.g. a human, mouse or gerbil, the condition of the subject, the size of the subject, etc. Thereafter, an animal so inoculated with the strain can be exposed to the bacterium to test the potential vaccine effect of the specific immunogenic protein or fragment.

For example, well-established models include gnotobiotic piglets and mice. The dapE⁻ mutant strain is first fed to the piglets or mice and maintained by DapE supplementation. After a suitable interval, the supplementation is stopped and the clearance of the vaccine strain is evaluated. Next, this piglet or mouse is challenged with a wild-type *H. pylori* strain or other microorganism and the presence or absence of infection is ascertained (48, 49). This same system can also be used to determine the amounts of mutant required to have a protective effect.

Once immunogenicity is established as described above, immunogenic amounts of the antigen can be determined using standard procedures. Briefly, various concentrations of the dapE⁻ mutant are prepared, administered to an animal and the immunological response (e.g., the production of antibodies) of an animal to each concentration is determined.

Pharmaceutically Acceptable Carrier

The pharmaceutically acceptable carrier in the vaccine of the instant invention can comprise saline or other suitable carriers (Arnon, R. (Ed.) *Synthetic Vaccines* I:83–92, CRC Press, Inc., Boca Raton, Fla., 1987). An adjuvant can also be a part of the carrier of the vaccine, in which case it can be selected by standard criteria based on the antigen used, the mode of administration and the subject (Arnon, R. (Ed.), 1987). Methods of administration can be by oral or sublingual means, or by injection, depending on the particular vaccine used and the subject to whom it is administered.

It can be appreciated from the above that the vaccine and immunization method can be used as a prophylactic or a therapeutic modality, for example, by inducing a therapeutic immune response. Thus, the invention provides methods of preventing or treating *H. pylori* infection and the associated diseases by administering the vaccine to a subject. Because the dapE⁻ mutant can contain and express many different foreign immunogens, the invention also provides methods of treating or preventing infections with other organisms.

DapE, GidA and ORF2 Proteins

A purified DapE protein of *Helicobacter pylori* is provided. The DapE protein can consist of the amino acid sequence defined in SEQ ID NO:4. A *H. pylori*-specific fragment of the DapE protein can be routinely obtained in accord with teaching herein and in the art, and is contemplated.

Similarly, the GidA protein and the protein encoded by ORF2 are provided in SEQ ID NOS:2 and 6.

EXAMPLES

Characterization of *Helicobacter pylori* dapE and construction of a conditionally lethal dapE⁻ mutant Bacterial Strains, Plasmids and Growth Conditions

*H. pylori* strain 60190 was used for the molecular cloning studies, and 21 well characterized clinical *H. pylori* strains from the Vanderbilt University Helicobacter/Campylobacter culture collection were used to determine the conservation of the cloned genes. Stock cultures were maintained at −70° C. in Brucella Broth (BBL Microbiology Systems, Cockysville, Md.) supplemented with 15% glycerol. *E. coli* DH5α, XL-1blue, and Dam⁻ strains were used for transformation, and pBluescript (Stratagene, La Jolla, Calif., USA) was used as a cloning vector. *E. coli* strains were routinely cultured in Luria-Bertani(LB) medium with shaking at 37° C., and the clinical *H. pylori* isolates were cultured on Trypticase soy agar plates containing 5% sheep blood in a microaerobic atmosphere, as described (13). For transformation of *H. pylori* (14), strains were grown at 37° C. in a microaerobic atmosphere on Brucella agar plates containing 5% Fetal Calf Serum (FCS) and 30 µg/ml kanamycin and supplements of 0 to 2 mM DAP (a racemic mixture of all three DAP isomers, Sigma Chemical Co, St. Louis, Mo.) or 1 mM lysine (Sigma).

Genetic Techniques and Nucleotide Sequence Analysis

Chromosomal DNA was prepared as described previously (40). All other standard molecular genetic techniques including Southern and colony hybridizations were performed, as described (24, 39). For molecular cloning, positive plaques were purified from a bank of approximately 5 kb random chromosomal fragments of *H. pylori* 60190 using ZapII and recombinant DNA was prepared as described (40). Restriction enzyme cleavage maps were generated, and a 5 kb fragment was subcloned into pBluescript to create pAK2 (FIG. 1). Another 5 kb fragment carrying a portion of the *H. pylori* genome overlapping only the orf2 region of pAK2 was subcloned into pBluescript to create pAK1 (FIG. 1). The nucleotide sequence was determined unambiguously on both strands using double-stranded DNA templates using an automated DNA sequencer (Perkin Elmer, Model ABI377, Foster City, Calif.) with the ThermoSequenase dye primer reaction kit (Amersham, Arlington Heights, Ill.). Oligonucleotide primers were synthesized at the Vanderbilt Cancer Center DNA core facility with an ABI 392 DNA synthesizer sequencer (Perkin Elmer). Nucleotide sequences were compiled and analyzed using programs in the GCG Package (16). Amplifications were conducted in a Perkin-Elmer Thermal Cycler. PCR conditions used in this study were 35 cycles of 94° C. for 1 min, 50° C. for 2 min, and 72° C. for 2 min, with a terminal extension at 72° C. for 10 min, and the primers used in this study are listed in Table 1.

TABLE 1

PCR Primers used in this study

| Designation | Gene | Position[a] | Strand | Length | Sequence | Reference |
|---|---|---|---|---|---|---|
| 1 | gidA | 569–586 | + | 18 | CAGGAAAAAGAGTGGTAA (SEQ ID No: 8) | This work |
| 2 | gidA | 2428–2445 | − | 18 | TTAAGAGTTTTTTCGCAA (SEQ ID No: 9) | This work |
| 3 | dapE | 2445–2462 | + | 18 | AAGGATATTTAATGAACG (SEQ ID No: 10) | This work |
| 4 | dapE | 3613–3633 | − | 21 | GTTTATTTATTTTATGCCTCA (SEQ ID No: 11) | This work |
| 5 | orf2 | 3801–3819 | + | 19 | TAATTTAGGCATAGAGAGC (SEQ ID No: 12) | This work |
| 6 | orf2 | 4024–4044 | + | 20 | TATAACGGACAAGGCGTATCT (SEQ ID No. 13) | This work |
| 7 | orf2 | 4429–4450 | − | 24 | GTTCTATTTTCAATTCCTTGAGAG (SEQ ID No. 14) | This work |
| 8 | orf3 | 5086–5103 | − | 18 | GCGTGAATGAATACGATA (SEQ ID No. 15) | This work |
| 9 | km | 689–712 | − | 24 | CTCCCACCAGCTTATATACCTTAG (SEQ ID No. 16) | 22 |
| 10 | km | 1336–1356 | + | 21 | CTGGGGATCAAGCCTGATTGG (SEQ ID No. 17) | 22 |
| 11 | km | 572–591 | − | 20 | GACCGTTCCGTGGCAAAGCA (SEQ ID No. 18) | 38 |
| 12 | km | 1601–1622 | + | 22 | CTTGTGCAATGTAACATCAGAG (SEQ ID No. 19) | 38 |
| 13 | gidA | 2300–2317 | + | 18 | GCATTCCAGGCTTAAGCT (SEQ ID No. 20) | This work |
| 14 | dapE | 2631–2650 | − | 20 | TGCATGTTCTTTTTCTGCAT (SEQ ID No. 21) | This work |
| 15 | dapE | 3506–3523 | + | 18 | GAGTTTGGCGTTATTAAT (SEQ ID No. 22) | This work |
| 16 | orf2 | 3850–3866 | − | 17 | GCTTTTTCAAAATGCGT (SEQ ID No. 23) | This work |
| 17 | vacA | 4116–4134 | − | 16 | AAGCTTGATCACTCC (SEQ ID No. 24) | 14 |

[a]Position in sequence shown in FIG. 2 except for km and vacA primers. Position refer to those in the cited publications.

Construction of Recombinant Plasmids with Insertion of Kanamycin-resistance Cassettes into Targeted Genes A *C. coli* km gene (22) was ligated into the unique BclI site of pAK2 within the gidA ORF to create pAK2:gidA:km (pME36) (FIG. 1). An *E. coli* km cassette from pUC4K (38) was inserted into the unique NdeI site within the dapE ORF to create pAK2:dapE:km (pMAK36) (FIG. 1). orf2 contained no unique sites for km insertion, but 3 HindIII sites were present within 107 bp. Therefore, to create orf2:km, the orf2 ORF from pAK1 was PCR-amplified and subcloned the amplified fragment into pT7Blue (Novagen, Madison, Wis.) to create pAK7. The 430 bp insert was subcloned into pCR-Script Cam SK (+), (Stratagene, La Jolla, Calif.), a pBluescript derivative encoding chloramphenicol resistance, to create pAK8. After HindIII digestion of pAK8, the km cassette from pUC4K was inserted into orf2 to create pAK8:orf2:km (pAKQ) (FIG. 1).

Construction of *H. pylori* dapE and orf2 Mutants

The constructs, pAK2:gidA:km (pME36), pAK2:dapE:km (pMAK36), or pAK8:orf2:km (pAKQ), all of which are unable to replicate in *H. pylori*, were introduced into *H. pylori* 60190 by natural transformation; pCTB8:km containing vacA:km was used as a positive control (14). The transformants were selected on Brucella broth agar plates containing 5% FCS and 30 μg/ml kanamycin. In certain experiments, plates were supplemented with 1 mM DAP to determine the conditions necessary for dapE⁻ mutant viability. To determine the minimum concentration needed for growth of the dapE⁻ mutant, strains were grown on media supplemented with 0 to 2.0 mM DAP or 1.0 mM lysine. To provide genetic evidence in the transformed strain of dapE disruption by the km insertion, DNA isolated from both the *H. pylori* mutant strain 60190 pAK2:dapE:km and wild-type strain 60190 was digested with BamHI and hybridized to dapE and km probes. The authenticity of the mutant strain also was verified by PCR, using primers based on dapE and km (FIG. 1 and Table 1). The authenticity of the orf2⁻ mutants also was verified by Southern hybridization and PCR using parallel methods.

Evidence of Homologous Recombination Between pAK2:gidA:km and *H. pylori* Strain 60190 Chromosomal DNA No viable gidA mutants were obtained, even with selection on media supplemented with DAP or lysine. To provide genetic evidence that double cross-over events had occurred during the pre-selective growth phase, allowing for the insertion of km in the *H. pylori* chromosome within gidA, PCR was performed with a forward primer specific for km (primer 10 in FIG. 1 and Table 1) and a reverse primer (primer 8 in FIG. 1 and Table 1) specific for a region of the *H. pylori* chromosome present in pAK1 that is beyond the fragment cloned in pAK2. DNA isolated from wild type strain 60190 was examined after overnight incubation with pAK2:gidA:km. As negative controls, DNA from wild type strain 60190 and a mixture of DNA from wild type strain 60190 and pAK2:gidA:km were used. As a positive control, the forward km primer (primer 10 in FIG. 1 and Table 1) and a confirmed vacA reverse primer (primer 17 in Table 1) (14) were tested on DNA isolated from wild type strain 60190 after overnight incubation with pCTB8:vacA:km.

RNA Isolation, Reverse Transcriptase-polymerase Chain Reaction (RT-PCR), and Slot-blot Analysis To determine whether gidA, dapE, and orf2 are co-transcribed, wild type and mutant *H. pylori* strains were cultured for 24 h on Brucella agar plates containing 5% FCS supplemented with 1 mM DAP, cells were harvested, and RNA was recovered for RT-PCR by two rounds of hot-phenol extraction, as described previously (40). cDNA was synthesized from log of DNAse-treated total RNA by priming with 1 μg of random hexamer (Pharmacia, Inc., Piscataway, N.J.), 1 mM of each dNTP, 20 units of RNAse inhibitor and AMV reverse transcriptase (Promega, Madison, Wis.) in a final volume of 20 ul at 42° C. for 15 min. PCR reactions were performed as described above.

Agarose gel electrophoresis was performed on specific RT-PCR amplified products from *H. pylori* wild-type and mutant strains using primers within gidA, dapE, or orf2 as follows: Lanes 1, 4, 7—wild type strain 60190; lanes 2, 5, 8—dapE⁻ mutant strain (60190E⁻); lanes 3, 6, 9—orf2⁻ mutant strain (60190-2⁻). PCR was performed using primers 13 and 14 and DNA (lanes 1–3), cDNA (lanes 4–6) or RNA (lanes 7–9) as templates. PCR was performed using primers 15 and 16 and DNA (lanes 1–3), cDNA (lanes 4–6) or RNA (lanes 7–9) as templates.

To provide further evidence that orf2 is co-transcribed with dapE, slot-blot RNA analysis of mRNA transcripts of gidA, dapE, and orf2 was used. DNAse-treated RNA samples (12 μg) from wild type(WT) *H. pylori* strain 60190, or its dapE⁻ or orf2⁻ mutants were transferred to nylon membranes, and hybridized with equal amounts (50,000 cpm) of radiolabelled cagA, gidA, dapE, or orf2 probes. Hybridization used probes specific for gidA (1.9 kb PCR-amplified gidA-specific fragment), dapE (1.1 kb PCR-amplified dapE-specific fragment), orf2 (0.7 kb PCR-amplified orf2-specific fragment), or cagA as positive control (0.5 kb PCR-amplified cagA-specific fragment). The amount of radiolabel (50,000 cpm) was standardized for each probe, and experiments were performed as previously described (32).

Isolation of *H. pylori* dapE

A 5 kb EcoRI genomic fragment from *H. pylori* strain 60190 was cloned into pBluescript to create pAK2 (FIG. 1), and the nucleotide sequence of this fragment was determined (FIG. 2). Analysis of translation of the 5050 bp nucleotide sequence in all possible reading frames revealed five complete or partial open reading frames (ORFs). The three complete ORFs, consisting of 1866, 1167, and 753 nucleotides, were oriented in the same direction and opposite to the partial ORFs present at the ends of the fragment (FIGS. 1 and 2). The first complete ORF begins with GTG as the initiation codon, and encodes a 621 amino acid polypeptide, yielding a predicted product with a 69,665 Da molecular mass. The second ORF begins with an ATG codon, 10 bp after the termination of the first ORF and encodes a 388 amino acid polypeptide, yielding a predicted 42,822 Da product. The third ORF begins with ATG 80 bp after the termination of the second ORF, and encodes a 250 amino acid polypeptide with a predicted molecular mass of 27,585 Da. Potential ribosome binding sites begin 6 or 7 bp upstream of each ORF. Upstream of the translational start of the first ORF is the sequence TATTTT, which resembles the consensus σ70–10 sequence (33), and is 19 bp downstream of the sequence TTGGCA that shares 5 of 6 bases with the corresponding −35 consensus sequence (33). Nucleotides 4456 to 4654 following the third ORF exhibit the sequence of a putative three-hairpin stem-loop structure (ΔG=−40.2) that could permit a strong mRNA transcriptional terminator. The single putative promoter and transcription terminator and the close location and orientation of the ORFs suggest that they may represent an operon.

Analysis of the Deduced Products of the ORFs

The translated amino acid sequence for genes in pAK2 was compared with databases using the FASTA, FASTDB, and BLAST network services of the National Center for Biotechnology Information. The deduced product from the first complete ORF showed significant homology throughout the translated amino acid sequence (48.3% identity and 66.5% similarity) with the glucose inhibited division protein, encoded by gidA in *E. coli* (9,36,43), *H. influenzae* (47.1% identity and 67.5% similarity) (18) (FIG. 3A), *Pseudomonas putida* (28) (47.9% identity and 68.9% similarity), and *Bacillus subtilis* (27,28) (46.1% identity and 64.4% similarity). The putative product of the second ORF showed significant homology (37.9% identity and 61.0% similarity) with N-Succinyl-L-diaminopimelic acid desuccinylase (encoded by dapE) of *E. coli* (7,45) (FIG. 3B) and *H. influenzae* (18) (39.1% identity and 58.8% similarity) (FIG. 3B). There was no substantial overall homology between the products of the other complete or the two incomplete ORFs and other known sequences. These genes are tentatively identified as orf1, orf2, and orf3, as shown in FIG. 1.

Conservation of gidA, dapE, and orf2 among *H. pylori* Strains

To determine whether other *H. pylori* strains possess sequences homologous to gidA, dapE, or orf2, 21 strains (10 cagA⁺ and 11 cagA⁻ strains) were studied by colony hybridization, using PCR-amplified gidA, dapE, and orf2 specific fragments. A positive signal was obtained from each of these strains, indicating that these genes are conserved in *H. pylori*, despite other genotypic variations.

Characterization of a dapE Mutant

To create a dapE mutant, *H. pylori* strain 60190 was transformed with pMAK36 (dapE:km), and plated transformants on kanamycin-containing medium including 1 mM DAP. Southern and PCR analysis of the kanamycin-resistant transformants indicated that the km cassette was stably incorporated into the single chromosomal dapE gene creating a dapE mutant. However, in repeated experiments, transformation of *H. pylori* with pMAK36 (dapE:km) on plates lacking DAP did not yield any transformants (Table 2). Similarly, the dapE⁻ mutants obtained on DAP-containing plates were unable to grow when re-plated on TSA agar or Brucella agar with 5% FCS without the addition of DAP. Transformation of *H. pylori* with pCTB8:vacA:km yielded a similar number of transformants whether or not DAP was present in the selective media and served as a positive control. The minimum DAP concentration required for survival of the dapE⁻ mutant was found to be 0.2 mM (Table 3). The dapE⁻ mutant was unable to grow on media supplemented with lysine only (Table 2), emphasizing the specific DAP requirement of *H. pylori* for growth and/or survival.

TABLE 2

Growth of wild type and mutant *H. pylori* strains on brucella agar in the presence or absence of DAP Medium[a]

| Strain | | DAP (1) lysine (−) | DAP (+)[b] lysine (−) | DAP (−) lysine (+)[c] |
|---|---|---|---|---|
| 60190 | | − | − | − |
| 60190 | vacA:km | + | + | + |
| 60190 | dapE:km | − | + | − |
| 60190 | orf2:km | + | + | + |

[a]Brucella broth with 1.5% agar supplemented with 5% FCS and 30 ug/ml kanamycin
[b]Additionally supplemented with 1 mM DAP in medium
[c]Additionally supplemented with 1 mM lysine in medium

TABLE 3

Minimum concentration of DAP required for growth of the dapE- *H. pylori* mutant

| DAP[a] | 2 mM | 1.5 mM | 1 mM | 0.5 mM | 0.2 mM | 0.1 mM | 0 mM |
|---|---|---|---|---|---|---|---|
| 60190 | − | − | − | − | − | − | − |
| 60190 dapE:km[b] 1 | + | + | + | + | + | − | − |
| 2 | + | + | + | + | + | + | − |
| 3 | + | + | + | + | + | + | − |
| 60190 vacA:km[2] 1 | + | + | + | + | + | + | + |
| 2 | + | + | + | + | + | + | + |
| 3 | + | + | + | + | + | + | + |

[a]DAP concentration in Brucella broth with 1.5% agar supplemented with 5% FCS and 30 ug/ml kanamycin
[b]3 mutant strains were tested
[c]3 mutant strains were tested

Characterization of an *H. pylori* Mutant Lacking orf2

The orf2 ORF begins only 80 bp downstream from dapE and lacks its own consensus promoter, suggesting that these genes could be co-transcribed and their products could be functionally related. To test this hypothesis, orf2 was disrupted by insertional mutagenesis, and demonstrated the authenticity of *H. pylori* mutant 60190 orf2:km by Southern hybridization and PCR. However, the orf2⁻ mutant was found to grow well with or without exogenous DAP in the growth medium (Table 2), demonstrating that orf2 is not required in the metabolic pathway leading to DAP formation.

Evidence that Mutation of gidA is Lethal in *H. pylori*

The dapE open reading frame is separated by only 10 bp from gidA, suggesting co-transcription and a functional relationship between these two genes. To determine whether the gidA product in *H. pylori* is associated with dapE synthesis, an attempt was made to insertionally inactivate gidA. However, efforts to inactivate gidA by transforming *H. pylori* strain 60190 with pAK2:gidA:km were unsuccessful. No transformants were observed even on media supplemented with DAP (or lysine), while parallel transformations that led to the inactivation of dapE or vacA yielded more than 100 transformants for each. Since these data suggested that interruption of gidA was lethal for *H. pylori*, PCR was performed to determine whether insertion of the kanamycin cassette within gidA had occurred to transiently create 60190 gidA:km, but this organism was not viable. As a positive control, wild type strain 60190 was incubated in parallel with pCTB8:vacA:km to create an insertion in vacA.

Agarose gel electrophoresis was performed on of PCR-amplified products from DNA isolated from wild type strain 60190 after overnight incubation and transformation with or without specified plasmid. All PCRs used a forward primer specific for km (primer 10 in FIG. 1 and Table 1). The reverse primer was either specific for a region of the *H. pylori* chromosome not included in the fragment cloned in pAK2 (primer 8 in FIG. 1 and Table 1) or was specific for vacA (primer 17 in Table 1) as a control. Lane 1: Template isolated from DNA strain 60190 after overnight incubation with pAK2:gidA:km, and primers 10 and 8. Lane 2: Template DNA isolated from strain 60190, and primers 10 and 8. Lane 3: Template is a mixture of DNA from strain 60190 and pAK2:gidA:km, and primers 10 and 8. Lane 4: Template: DNA from strain 60190 after overnight incubation with pCTB8:vacA:km, and primers 10 and 17.

When the forward km primer (primer 10 in FIG. 1 and Table 1) and reverse vacA primer (primer 17 in Table 1) were used, a 3.1 kb band was amplified, as expected. Using a forward km primer (primer 10) and a reverse primer (primer 8 in FIG. 1 and Table 1) that is not present in pAK2 (FIG. 1), a 4.2 kb band was amplified in DNA isolated from wild type strain 60190 that had been incubated overnight with pAK2:gidA:km. No band was present in DNA from wild type strain 60190 alone, or if 60190 DNA was mixed with pAK2:gidA:km in the absence of *H. pylori* cells.

These results indicate that homologous recombination had occurred between the chromosomal DNA of the wild type strain 60190 and pAK2:gidA:km leading to km insertion within gidA, and provided further evidence that this transformation event was lethal to *H. pylori*.

RT-PCR and Slot-blot Analysis

To ascertain whether gidA, dapE, and orf2 are co-transcribed, RNA was extracted for analysis from wild type *H. pylori* strain 60190 and its dapE⁻ and orf2⁻ mutants. Reverse transcriptase-PCR (RT-PCR) of cDNA template was performed with a pair of primers bridging the gidA and dapE ORFs (primers 13 and 14, Table 1).

A 0.35 kb product was detected for each strain, as expected. In RT-PCR using primers bridging the dapE-orf2 ORFs (primers 15 and 16), no product was detected in the dapE mutant, as expected, but both the wild type strain and the orf2 mutant showed a product of the expected size (0.4 kb). Negative-control PCR using RNA as template showed no products. As expected, the positive control cagA probe hybridized with equal intensity to the wild type strain and its dapE and orf2 mutants. The gidA probe hybridized to RNA with similar intensity for the wild type strain and its dapE⁻ and orf2⁻ mutants. The dapE probe hybridized equally well to wild type and orf2⁻ mutant RNA, and less well to its dapE⁻ mutant. The orf2 probe hybridized well to RNA in the wild type strain, but only weakly to RNA from the dapE and orf2 mutants. The results of both sets of experiments indicate that orf2 can be co-transcribed with dapE.

The results in this study suggest that the ability of *H. pylori* to synthesize DAP is based only on the succinylase pathway, or that its synthesis via the dehydrogenase and/or acetylase pathways is too low to allow for survival.

The gidA, dapE, and orf2 ORFs are closely spaced and oppositely oriented to the flanking genes (FIG. 1), suggesting that they form an operon. A sequence bearing strong homology to the $\sigma^{70}$ promoter is present 5' to gidA, but no promoter-like elements were observed upstream of dapE and orf2. The presence of a strong putative transcriptional terminator downstream of orf2 also is consistent with the notion that these 3 genes form an operon, and RT-PCR and slot blot data indicate that dapE and orf2 may be co-transcribed. The presence of another putative transcriptional terminator, an 80-nucleotide palindromic sequence (DG=−2.9), beginning at nucleotide 3623 to 3702 in the intergenic region between dapE and orf2, may, under certain conditions, allow for transcription of gidA and dapE without orf2.

The dapE ORF is separated by only 10 bp from gidA. In *E. coli*, gidA lies near the origin of replication (oriC) (29); inactivation of gidA by transposon insertion reduces the *E. coli* growth rate by 20% and causes filamentation of cells in media containing glucose (41, 42). However, in *H. pylori*, the arrangement of gidA and dapE in the same operon suggests that the products of these two genes could be functionally related. However, the inability of DAP or lysine supplementation to permit gidA mutants to survive suggests that its critical activity does not involve the DAP/lysine pathway.

The presence of orf2 80 bp downstream from dapE, with no unique promoter sequence, suggests that these two genes may be co-transcribed and that their protein products may be functionally related. RT-PCR and slot-blot results support this hypothesis, since orf2 RNA was not transcribed in the dapE⁻ mutant. That the orf2⁻ mutant strain grew normally without exogenous DAP indicates that the orf2 product is not required for DAP biosynthesis.

The observations made in this study suggest that the enzymes involved in DAP biosynthesis represent targets for the development of novel agents against *H. pylori* (3,4,20, 21). DAP biosynthetic genes also may be used to stabilize shuttle plasmids for use in *H. pylori* in the absence of antibiotic markers (25). If *H. pylori* strains carrying mutations in DAP biosynthesis genes can be constructed, plasmids carrying the respective complementing gene could be maintained. Such plasmids may lead to the ability to stably maintain recombinant DNA in humans for the expression of

*H. pylori* or heterologous antigens, and may provide tools in the investigation of *H. pylori* pathogenesis as well as for the development of new anti-*H. pylori* agents.

These results also suggest that co-administration of *H. pylori* dapE⁻ mutant strains with a DAP supplement may serve as an immunization strategy. After sufficient time for evoking an immune response directed at this *H. pylori* strain, cessation of DAP supplementation would lead to its death. Ideally, optimal timing of supplementation could result in the establishment of long-term immunity to *H. pylori* or to heterologous antigens delivered by this superb mucosal colonizer.

Throughout this application various publications are referenced by numbers within parentheses. Full citations for these publications are as follows. The disclosures of these publications in their entireties are hereby incorporated by reference into this application in order to more fully describe the state of the art to which this invention pertains.

References

1. Akopyants, N. S., D. Kersulyte, and D. E. Berg. 1995. CagII, a new multigene locus associated with virulence in *Helicobacter pylori*. Gut 37:A1
2. Barlett, A. T. M. and P. J. White. 1985. Species of bacillus that make a vegetative peptidoglycan containing lysine lack diaminopimelate epimerase but have diaminopimelate dehydrogenase. J. Gen. Microbiol. 131:2145–2152.
3. Barlett, P. A. and C. K. Marlowe. 1983. Phosphonamidates as transition-state analogue inhibitors of thermolysin. Biochemistry 22:4618–4624.
4. Berges, D. A., W. E. DeWolf, Jr., G. L. Dunn, S. F. Grappel, D. J. Newman, J. J. Taggart, and C. Gilvarg. 1986. Peptides of 2-aminopimelic acid: antibacterial agents that inhibit diaminopimelic acid. J. Med. Chem. 29:85–89.
5. Blaser, M. J., G. I. Pérez-Pérez, H. Kleanthous, T. L. Cover, R. M. Peek, P. H. Chyou, G. N. Stemmermann, and A. Nomura. 1995. Infection with *Helicobacter pylori* strains possessing cagA associated with an increased risk of developing adenocarcinoma of the stomach. Cancer Res. 55:2111–2115.
6. Blaser, M. J., G. I. Pérez-Pérez, J. Lindenbaum, D. Schneidman, G. Van Deventer, M. Marin-Sorensen, and W. M. Weinstein. 1991. Association of infection due to *Helicobacter pylori* with specific upper gastrointestinal pathology. Rev. Infect. Dis. 13:S704–S708.
7. Bouvier, J., C. Richaud, W. Higgins, O. Bogler, and P. Stragier. 1992. Cloning, characterization, and expression of the dapE gene of *Escherichia coli*. J. Bacteriol. 174:5265–5271.
8. Bukhari, A. I. and A. L. Taylor. 1971. Genetic analysis of diaminopimelic acid- and lysine-requiring mutants of *Escherichia coli*. J. Bacteriol. 105:844–854.
9. Burland, V., G. Plunkett,III, D. L. Daniels, and F. R. Blattner. 1993. DNA sequence and analysis of 136 kilobases of the *Escherichia coli* genome: organizational symmetry around the origin of replication. Genomics 16:551–561.
10. Cirillo, J. D., T. R. Weisbrod, A. Banarjee, B. R. Bloom, and Jacobs, Jr. 1994. Genetic determination of the meso-Diaminopimelate biosynthetic pathway of mycobacteria. J. Bacteriol. 176:4424–4429.
11. Covacci, A., S. Censini, M. Bugnoli, R. Petracca, D. Burroni, G. Macchia, A. Massone, E. Papini, Z. Xiang, N. Figura, and et al. 1993. Molecular characterization of the 128-kDa immunodominant antigen of *Helicobacter pylori* associated with cytotoxicity and duodenal ulcer. Proc. Natl. Acad. Sci. U. S. A. 90:5791–5795.
12. Cover, T. L., Y. Glupczynski, A. P. Lage, A. Burette, M. K. R. Tummuru, G. I. Pérez-Pérez, and M. J. Blaser. 1995. Serologic detection of infection with cagA⁺ *Helicobacter pylori* strains. J. Clin. Microbiol. 33:1496–1500.
13. Cover, T. L., W. Puryear, G. I. Pérez-Pérez, and M. J. Blaser. 1991. Effect of urease on HeLa cell vacuolation induced by *Helicobacter pylori* cytotoxin. Infect. Immun. 59:1264–1270.
14. Cover, T. L., M. K. R. Tummuru, P. Cao, S. A. Thompson, and M. J. Blaser. 1994. Divergence of genetic sequences for the vacuolating cytotoxin among *Helicobacter pylori* strains. J. Biol. Chem. 269:10566–10573.
15. Crabtree, J. E., J. D. Taylor, J. I. Wyatt, R. V. Heatley, T. M. Shallcross, D. S. Tompkins, and B. J. Rathbone. 1991. Mucosal IgA recognition of *Helicobacter pylori* 120 kDa protein, peptic ulceration, and gastric pathology. Lancet 338:332–335.
16. Devereux, J., P. Haeberli, and O. Smithies. 1984. A comprehensive set of sequence analysis programs for the VAX. Nucleic Acids Res. 12:387–395.
17. Dewey, D. and E. Work. 1952. Diaminopimelic acid decarboxylase. Nature 169:533–534.
18. Fleischmann, R. D., M. D. Adams, O. White, R. A. Clayton, E. F. Kirkness, A. R. Kerlavage, C. J. Bult, J. F. Tomb, B. A. Dougherty, J. M. Merrick, K. McKenney, G. Sutton, W. Fitzhugh, C. A. Fields, J. D. Gocayne, J. D. Scott, R. Shirley, L. I. Liu, A. Glodek, J. M. Kelley, J. F. Weidman, C. A. Phillips, T. Spriggs, E. Hedblom, M. D. Cotton, T. R. Utterback, M. C. Hanna, D. T. Nguyen, D. M. Saudek, R. C. Brandon, L. D. Fine, J. L. Fritchman, J. L. Fuhrmann, N. S. M. Geoghagen, C. L. Gnehm, L. A. McDonald, K. V. Small, C. M. Fraser, H. O. Smith, and J. C. Venter. 1995. Whole-genome random sequencing and assembly of *Haemophilus influenza* Rd. Science 269:469–512.
19. Galan, J. E., K. Nakayama, and R. Curtiss,III. 1990. Cloning and characterization of the asd gene of *Salmonella typhimurium*: use in stable maintenance of recombinant plasmids in Salmonella vaccine strains. Gene 94:29–35.
20. Galardy, R. E. and Z. P. Kortylewicz. 1984. Inhibition of Carboxypeptidase A by aldehyde and ketone substrate analogues. Biochemistry 23:2083–2087.
21. Gelb, M. H., J. P. Svaren, and R. H. Abeles. 1985. Fluoro ketone inhibitors of hydrolytic enzymes. Biochemistry 24:1813–1817.
22. Labigne-Roussel, A., J. Harel, and L. Tompkins. 1987. Gene transfer from *Escherichia coli* to Campylobacter species. Development of shuttle vectors for genetic analysis of *Campylobacter jejuni*. J. Bacteriol. 169:5320–5323.
23. Lin, Y., R. Myhrman, M. L. Schrag, and M. H. Gelb. 1987. Bacterial N-succinyl-L-diaminopimelic acid desuccinylase. J. Biol. Chem. 1622–1627.
24. Maniatis, T., E. F. Fritsch, and J. Sambrook. 1989. Molecular cloning; a laboratory manual. Cold Spring Harbor Laboratory, Cold Spring Harbor, N.Y.
25. Nakayama, K., S. M. Kelley, and R. Curtiss,III. 1988. Construction of an asd expression-cloning vector: stable maintenance and high level expression of cloned genes in a salmonella vaccine strain. Bio. Technol. 6:693–697.
26. Nomura, A., G. N. Stemmermann, P. Chyou, I. Kato, G. I. Pérez-Pérez, and M. J. Blaser. 1991. *Helicobacter pylori* infection and gastric carcinoma in a population of Japanese-Americans in Hawaii. N. Engl. J. Med. 325:1132–1136.
27. Ogasawara, N., S. Nakai, and H. Yoshiokawa. 1994. Systematic sequencing of the 180 kilobase region of the 28. Ogasawara, N. and H. Yoshikawa. 1992. Genes and their organization in the replication origin region of the bacterial chromosome. Mol. Microbiol. 6:629–634.
29. Ogawa, T. and T. Okazaki. 1994. Cell cycle-dependent transcription from the gid and mioC promoters of *Escherichia coli*. J. Bacteriol. 176:1609–1615.
30. Parsonnet, J., G. D. Friedman, D. P. Vandersteen, Y. Chang, J. H. Vogelman, N. Orentreich, and R. K. Sibley. 1991. *Helicobacter pylori* infection and the risk of gastric carcinoma. N. Engl. J Med 325:1127–1131.
31. Patte, J. C. 1996. Biosynthesis of Threonine and lysine, p. 532–535. In F. C. Neidhardt (ed.), *Escherichia coli* and Salmonella, cellular and molecular biology. ASM Press, Washington, D.C.
32. Peek, R. M., Jr., S. A. Thompson, J. C. Atherton, M. J. Blaser, and G. G. Miller. 1996. Expression of a novel ulcer-associated *H. pylori* gene, iceA, after contact with gastric epithelium. Gastroenterol. (In Press)
33. Rosenberg, M. and D. Court. 1979. Regulatory sequences involved in the promotion and termination of RNA transcription. ( ) 13:319–353.
34. Schrumpf, B., A. Schwarzer, J. Kalinowski, A. Puhler, L. Eggeling, and H. Sahm. 1991. A functionally split pathway for lysine synthesis in *Corynebacterium glutamicum*. J. Bacteriol. 173:4510–4516.
35. Stragier, P., O. Danos, and J. C. Patte. 1983. Regulation of diaminopimelate decarboxylase synthesis in *Escherichia coli* III. Nucleotide sequence of the lysA gene and its regulatory region. J. Mol. Biol. 168:321–331.
36. Sugimoto, K., A. Oka, H. Sugisaki, M. Takanami, A. Nishimura, Y. Yasuda, and Y. Hirota. 1979. Nucleotide sequence of *Escherichia coil K-12* replication origin. Proc. Natl. Acad. Sci. U. S. A. 76:575–579.
37. Talley, N. J., A. R. Zinsmeister, E. P. Dimagno, A. Weaver, H. A. Carpenter, G. I. Pérez-Pérez, and M. J. Blaser. 1991. Gastric adenocarcinoma and *Helicobacter pylori* infection. J. Nat. Cancer Instit. 83:1734–1739.
38. Tayor, L. A. and R. E. Rose. 1988. A correction in the nucleotide sequence of Tn 903 kanamycin resistance determinant in pUC4K. Nucleic Acids Res. 16:358–368.
39. Tummuru, M. K. R., T. L. Cover, and M. J. Blaser. 1993. Cloning and expression of a high molecular weight major antigen of *Helicobacter pylori*: evidence of linkage to cytotoxin production. Infect. Immun. 61:1799–1809.
40. Tummuru, M. K. R., S. A. Sharma, and M. J. Blaser. 1995. *Helicobacter pylori* picB, a homolog of the *Bordetelia pertussis* toxin secretion protein, is required for induction of IL-8 in gastric epithelial cells. Mol. Microbiol. 18:867–876.
41. von Meyenburg, K. and F. G. Hansen. 1980. The origin or replication, oriC, of the *Escherichia coli* chromosome: genes near oriC and construction of oriC deletion mutations. Mol. Cell. Biol. 19:137–159.
42. von Meyenburg, K., B. B. Jorgensen, J. Nielsen, and F. G. Hansen. 1982. Promoters of the atp operon coding for the membrane-bound ATP synthase *Escherichia coli* mapped by Tn10 insertion mutations. Mol. Gen. Genet. 188:240–248.
43. Walker, J. E., N. J. Gay, M. Saraste, and A. N. Eberle. 1984. DNA sequence around the *Escherichia coli* unc operon. Completion of the sequence of a 17 kilobase segment containing asnA, oriC, unc, glmS, and phoS. Biochem. J. 224:799–815.
44. Weinberger, S. and C. Gilvarg. 1970. Bacterial distribution of the use of succinyl and acetyl blocking groups in diaminopimelic acid biosynthesis. J. Bacteriol. 101:323–324.
45. Wu, B., C. Georgopoulos, and D. Ang. 1992. The essential *Escherichia coli* msgB gene, a multicopy suppressor of a temperature-sensitive allele of the heat shock gene grpE, is identical to dapE. J. Bacteriol. 174:5258–5264.
46. McKnight, S. L. and R. Kingsbury (1982) Transcriptional control signals of a eukaryotic protein-coding gene. Science 217:316.
47. Kunkel, T. A. (1985) Rapid and efficient site-specific mutagenesis without phenotypic selection. Proc. Natl. Acad. Sci. 82:488 (1985) Rapid and efficient site-specific mutagenesis without phenotypic selection. Proc. Natl. Acad. Sci. 82:488
48. Eaton, J. A., C. L. Brooks, D. R. Morgan, and S. Krawowka (1991). Essential role of urease in pathogenesis of gastritis induced by *Helicobacter pylori* in gnotobiotic piglets. Infect. Immun. 59:2470–5.
49. Eaton, K. A., D. R. Morgan and S. Krakowka (1992) Motility as a factor in the colonisation of gnotobiotic piglets by *Helicobacter pylori*. J. Med. Microbiol. 37:123–7.

What is claimed is:

1. An isolated nucleic acid consisting of the nucleotide sequence of SEQ ID NO:3.

2. A vector comprising the nucleic acid of claim 1.

3. An Helicobacter pylori-specific nucleic acid fragment comprising 90 consecutive nucleotides of SEQ ID NO 3.

4. An isolated nucleic acid that encodes a naturally occurring N-succinyl-L-diaminopimelic acid desuccinylase (DapE) protein of Helicobacter pylori and hybridizes over its full length with the complement of the nucleic acid of SEQ ID NO:3 under the stringency conditions of about 16 hrs at about 65° C., about 5×SSC, about 0.1% SDS, about 2×Denhardt's solution, about 150 µg/ml salmon sperm DNA with washing at about 65° C., 30 min, 2×, in about 0.1× SSPE/0.1% SDS, wherein the nucleic acid is at least 96% complementary to the complement of the nucleic acid of SEQ ID NO:3.

5. A vector comprising the nucleic acid of claim 4.

6. An isolated nucleic acid that hybridizes with the nucleic acid of SEQ ID NO:3 under the stringency conditions of about 16 hrs at about 65° C., about 5×SSC, about 0.1% SDS, about 2×Denhardt's solution, about 150 µg/ml salmon sperm DNA with washing at about 65° C., 30 min, 2×, in about 0.1×SSPE/0.1% SDS, wherein the nucleic acid specifically identifies a Helicobacter pylori dapE nucleic acid, is 25 to 380 or 400 to 1160 nucleotides in length, and is at least 95% complementary to SEQ ID NO:3.

7. A vector comprising the nucleic acid of claim 6.

8. An isolated nucleic acid that hybridizes with the nucleic acid of SEQ ID NO:3 under the stringency conditions of 35 cycles of 94° C. for 1 min, 50° C. for 2 min, and 72° C. for 2 min, with a terminal extension at 72° C. for 10 min, wherein the nucleic acid amplifies only a Helicobacter pylori dapE nucleic acid, is 25 to 380 or 400 to 1160 nucleotides in length, and is at least 95% complementary co SEQ ID NO:3.

9. A vector comprising the nucleic acid of claim 8.

10. A purified mutant strain of *Helicobacter pylori* having a mutated genome that does not express a functional DapE protein, wherein the mutant strain contains a plasmid comprising a nucleic acid that encodes and expresses a functional *H. pylori* DapE protein.

11. The mutant strain of claim 10, wherein the nucleic acid that encodes and expresses a functional *H. pylori* DapE protein hybridizes over its full length with the complement of the nucleic acid of SEQ ID NO:3 under the stringency conditions of about 16 hrs at about 65° C., about 5×SSC, about 0.1% SDS, about 2×Denhardt's solution, about 150 μg/ml salmon sperm DNA with washing at about 65° C., 30 min, 2×, in about 0.1×SSPE/0.1% SDS, wherein the nucleic acid is at least 95% complementary t,o the complement of the nucleic acid of SEQ ID NO:3.

12. An isolated nucleic acid encoding the polypeptide of SEQ ID NO:29.

13. A vector comprising the nucleic acid of claim 12.

* * * * *

SEQUENCE LISTING

<160> NUMBER OF SEQ ID NOS: 30

<210> SEQ ID NO 1
<211> LENGTH: 1866
<212> TYPE: DNA
<213> ORGANISM: Artificial Sequence
<220> FEATURE:
<221> NAME/KEY: CDS
<222> LOCATION: (1)...(1863)
<223> OTHER INFORMATION: Description of Artificial Sequence:/ Note = synthetic construct

<400> SEQUENCE: 1

```
gtg gta aaa gaa agt gat att tta gtg att ggt ggg ggg cat gcg ggc      48
Val Val Lys Glu Ser Asp Ile Leu Val Ile Gly Gly Gly His Ala Gly
 1               5                  10                  15
```

```
att gaa gcg agc ttg att gca gcc aaa atg ggg gct agg gtg cat tta      96
Ile Glu Ala Ser Leu Ile Ala Ala Lys Met Gly Ala Arg Val His Leu
         20                  25                  30 atc acc atg ctc ata gac acg atc ggt tta gcg agc tgt aac ccg gcg     144
Ile Thr Met Leu Ile Asp Thr Ile Gly Leu Ala Ser Cys Asn Pro Ala
     35                  40                  45 att ggg ggc ttg ggt aaa ggg cat ttg act aaa gaa gtg gat gtt tta     192
Ile Gly Gly Leu Gly Lys Gly His Leu Thr Lys Glu Val Asp Val Leu
 50                  55                  60 ggg ggg gct atg ggg att att aca gat cat agc ggt ttg caa tat cgt     240
Gly Gly Ala Met Gly Ile Ile Thr Asp His Ser Gly Leu Gln Tyr Arg
 65                  70                  75                  80 gtg tta aac gct tct aaa ggg ccg gcg gtt agg ggg act aga gcg caa     288
Val Leu Asn Ala Ser Lys Gly Pro Ala Val Arg Gly Thr Arg Ala Gln
             85                  90                  95 att gat atg gat act tac cgc att ttt gca aga aat ctt gtt tta aac     336
Ile Asp Met Asp Thr Tyr Arg Ile Phe Ala Arg Asn Leu Val Leu Asn
        100                 105                 110 acc cct aat ttg agc gtc tct caa gaa atg acc gaa agt tta atc ctt     384
Thr Pro Asn Leu Ser Val Ser Gln Glu Met Thr Glu Ser Leu Ile Leu
        115                 120                 125 gaa aac gat gag gta gtg ggc gta acc acg aac att aat aac act tac     432
Glu Asn Asp Glu Val Val Gly Val Thr Thr Asn Ile Asn Asn Thr Tyr
130                 135                 140 aga gct aaa aaa gtg atc atc acc aca ggc act ttt tta aaa ggg gtg     480
Arg Ala Lys Lys Val Ile Ile Thr Thr Gly Thr Phe Leu Lys Gly Val
145                 150                 155                 160 gtg cat att ggc gag cac caa aac caa aac ggg cgt ttt ggg gaa aac     528
Val His Ile Gly Glu His Gln Asn Gln Asn Gly Arg Phe Gly Glu Asn
                165                 170                 175 gct tcc aat tct tta gcc ttg aat tta agg gag ctt ggc ttt aag gtg     576
Ala Ser Asn Ser Leu Ala Leu Asn Leu Arg Glu Leu Gly Phe Lys Val
            180                 185                 190 gag agg tta aaa acc ggc act tgc cca aga gtg gcc ggc aat agc att     624
Glu Arg Leu Lys Thr Gly Thr Cys Pro Arg Val Ala Gly Asn Ser Ile
        195                 200                 205 gat ttt gaa ggc tta gaa gag cat ttt ggg gat gca aac cct ccc tat     672
Asp Phe Glu Gly Leu Glu Glu His Phe Gly Asp Ala Asn Pro Pro Tyr
210                 215                 220 ttc agc tat aaa acc aaa gat ttt aac ccc acc caa ctc tct tgt ttc     720
Phe Ser Tyr Lys Thr Lys Asp Phe Asn Pro Thr Gln Leu Ser Cys Phe
225                 230                 235                 240 atc act tac act aac ccc att acc cac caa atc att agg gat aat ttc     768
Ile Thr Tyr Thr Asn Pro Ile Thr His Gln Ile Ile Arg Asp Asn Phe
                245                 250                 255 cac cga gct ccc ctt ttt agc ggt caa att gaa ggc ata ggc cca agg     816
His Arg Ala Pro Leu Phe Ser Gly Gln Ile Glu Gly Ile Gly Pro Arg
            260                 265                 270 tat tgc cct agc att gaa gat aaa atc aac cgc ttt agt gaa aaa gaa     864
Tyr Cys Pro Ser Ile Glu Asp Lys Ile Asn Arg Phe Ser Glu Lys Glu
        275                 280                 285 cgc cac cag ctg ttt tta gag cct caa acc att cat aaa aac gaa tat     912
Arg His Gln Leu Phe Leu Glu Pro Gln Thr Ile His Lys Asn Glu Tyr
        290                 295                 300 tat atc aac ggc tta agc acc tct ttg ccc cta gat gtg caa gaa aag     960
Tyr Ile Asn Gly Leu Ser Thr Ser Leu Pro Leu Asp Val Gln Glu Lys
305                 310                 315                 320 gtc att cat tct atc aaa ggc tta gaa aac gcc ctc atc acg cgc tat    1008
Val Ile His Ser Ile Lys Gly Leu Glu Asn Ala Leu Ile Thr Arg Tyr
```

```
                        325                 330                 335
ggc tat gcg ata gag tat gat ttc atc cag cct aca gaa tta acc cac      1056
Gly Tyr Ala Ile Glu Tyr Asp Phe Ile Gln Pro Thr Glu Leu Thr His
            340                 345                 350 gct tta gaa acc aaa aaa atc aaa ggg ctt tat ttg gcc ggg caa atc      1104
Ala Leu Glu Thr Lys Lys Ile Lys Gly Leu Tyr Leu Ala Gly Gln Ile
        355                 360                 365 aat ggg act acc ggc tat gaa gaa gcg gcg gat caa ggg ctt atg gct      1152
Asn Gly Thr Thr Gly Tyr Glu Glu Ala Ala Asp Gln Gly Leu Met Ala
    370                 375                 380 ggg att aat gcg gta tta gcc tta aag aat caa gcc ccc ttt att tta      1200
Gly Ile Asn Ala Val Leu Ala Leu Lys Asn Gln Ala Pro Phe Ile Leu
385                 390                 395                 400 aag cgc aat gaa gct tat att ggc gtt ttg att gat gat ttg gtt act      1248
Lys Arg Asn Glu Ala Tyr Ile Gly Val Leu Ile Asp Asp Leu Val Thr
                405                 410                 415 aaa ggc acg aat gag cct tac aga atg ttt act agc cga gcc gaa tac      1296
Lys Gly Thr Asn Glu Pro Tyr Arg Met Phe Thr Ser Arg Ala Glu Tyr
            420                 425                 430 cgc ttg ctt tta aga gag gac aac acg ctt ttt agg ttg ggc gaa cat      1344
Arg Leu Leu Leu Arg Glu Asp Asn Thr Leu Phe Arg Leu Gly Glu His
        435                 440                 445 gcc tat cgt tta ggg ctt atg gaa cag gat ttt tat aag gaa tta aaa      1392
Ala Tyr Arg Leu Gly Leu Met Glu Gln Asp Phe Tyr Lys Glu Leu Lys
    450                 455                 460 aaa gat aaa caa gag ata caa gac aat ctc aaa cgc ctt aaa gaa tgc      1440
Lys Asp Lys Gln Glu Ile Gln Asp Asn Leu Lys Arg Leu Lys Glu Cys
465                 470                 475                 480 gtc ctt acc cct agt aaa aaa ttg tta aaa cgc ttg aac gaa tta gac      1488
Val Leu Thr Pro Ser Lys Lys Leu Leu Lys Arg Leu Asn Glu Leu Asp
                485                 490                 495 gaa aac cct atc aat gac aag gtt aat ggc gtt agt ttg tta gca cgc      1536
Glu Asn Pro Ile Asn Asp Lys Val Asn Gly Val Ser Leu Leu Ala Arg
            500                 505                 510 gat agt ttt aat gca gaa aaa atg cgc tcc ttt ttc agc ttt tta gcc      1584
Asp Ser Phe Asn Ala Glu Lys Met Arg Ser Phe Phe Ser Phe Leu Ala
        515                 520                 525 ccc ttg aac gag cgg gtt tta gag cag att aaa att gaa tgc aaa tat      1632
Pro Leu Asn Glu Arg Val Leu Glu Gln Ile Lys Ile Glu Cys Lys Tyr
    530                 535                 540 aat att tat att gaa aag caa cac gaa aat atc gct aaa atg gat agc      1680
Asn Ile Tyr Ile Glu Lys Gln His Glu Asn Ile Ala Lys Met Asp Ser
545                 550                 555                 560 atg ctc aaa gtt tct atc cct aaa ggt ttt gtg ttt aaa ggc att cca      1728
Met Leu Lys Val Ser Ile Pro Lys Gly Phe Val Phe Lys Gly Ile Pro
                565                 570                 575 ggc tta agc tta gaa gcg gta gaa aaa tta gaa aaa ttc cgc ccc aaa      1776
Gly Leu Ser Leu Glu Ala Val Glu Lys Leu Glu Lys Phe Arg Pro Lys
            580                 585                 590 agc ctt ttt gaa gcc tca gaa atc agc ggg atc act cca gcg aat tta      1824
Ser Leu Phe Glu Ala Ser Glu Ile Ser Gly Ile Thr Pro Ala Asn Leu
        595                 600                 605 gac gtt ttg cat tta tac atc cat ttg cga aaa aac tct taa              1866
Asp Val Leu His Leu Tyr Ile His Leu Arg Lys Asn Ser
    610                 615                 620

<210> SEQ ID NO 2
<211> LENGTH: 621
<212> TYPE: PRT
<213> ORGANISM: Artificial Sequence
```

```
<220> FEATURE:
<223> OTHER INFORMATION: Description of Artificial Sequence:-ote =
      synthetic construct

<400> SEQUENCE: 2

Val Val Lys Glu Ser Asp Ile Leu Val Ile Gly Gly His Ala Gly
 1               5                  10                  15

Ile Glu Ala Ser Leu Ile Ala Ala Lys Met Gly Ala Arg Val His Leu
            20                  25                  30

Ile Thr Met Leu Ile Asp Thr Ile Gly Leu Ala Ser Cys Asn Pro Ala
            35                  40                  45

Ile Gly Gly Leu Gly Lys Gly His Leu Thr Lys Glu Val Asp Val Leu
            50                  55                  60

Gly Gly Ala Met Gly Ile Ile Thr Asp His Ser Gly Leu Gln Tyr Arg
65                  70                  75                  80

Val Leu Asn Ala Ser Lys Gly Pro Ala Val Arg Gly Thr Arg Ala Gln
            85                  90                  95

Ile Asp Met Asp Thr Tyr Arg Ile Phe Ala Arg Asn Leu Val Leu Asn
            100                 105                 110

Thr Pro Asn Leu Ser Val Ser Gln Glu Met Thr Glu Ser Leu Ile Leu
            115                 120                 125

Glu Asn Asp Glu Val Val Gly Val Thr Thr Asn Ile Asn Asn Thr Tyr
            130                 135                 140

Arg Ala Lys Lys Val Ile Ile Thr Thr Gly Thr Phe Leu Lys Gly Val
145                 150                 155                 160

Val His Ile Gly Glu His Gln Asn Gln Asn Gly Arg Phe Gly Glu Asn
            165                 170                 175

Ala Ser Asn Ser Leu Ala Leu Asn Leu Arg Glu Leu Gly Phe Lys Val
            180                 185                 190

Glu Arg Leu Lys Thr Gly Thr Cys Pro Arg Val Ala Gly Asn Ser Ile
            195                 200                 205

Asp Phe Glu Gly Leu Glu Glu His Phe Gly Asp Ala Asn Pro Pro Tyr
            210                 215                 220

Phe Ser Tyr Lys Thr Lys Asp Phe Asn Pro Thr Gln Leu Ser Cys Phe
225                 230                 235                 240

Ile Thr Tyr Thr Asn Pro Ile Thr His Gln Ile Arg Asp Asn Phe
            245                 250                 255

His Arg Ala Pro Leu Phe Ser Gly Gln Ile Glu Gly Ile Gly Pro Arg
            260                 265                 270

Tyr Cys Pro Ser Ile Glu Asp Lys Ile Asn Arg Phe Ser Glu Lys Glu
            275                 280                 285

Arg His Gln Leu Phe Leu Glu Pro Gln Thr Ile His Lys Asn Glu Tyr
            290                 295                 300

Tyr Ile Asn Gly Leu Ser Thr Ser Leu Pro Leu Asp Val Gln Glu Lys
305                 310                 315                 320

Val Ile His Ser Ile Lys Gly Leu Glu Asn Ala Leu Ile Thr Arg Tyr
            325                 330                 335

Gly Tyr Ala Ile Glu Tyr Asp Phe Ile Gln Pro Thr Glu Leu Thr His
            340                 345                 350

Ala Leu Glu Thr Lys Lys Ile Lys Gly Leu Tyr Leu Ala Gly Gln Ile
            355                 360                 365

Asn Gly Thr Thr Gly Tyr Glu Glu Ala Ala Asp Gln Gly Leu Met Ala
            370                 375                 380

Gly Ile Asn Ala Val Leu Ala Leu Lys Asn Gln Ala Pro Phe Ile Leu
```

```
                385                 390                 395                 400
Lys Arg Asn Glu Ala Tyr Ile Gly Val Leu Ile Asp Asp Leu Val Thr
                    405                 410                 415

Lys Gly Thr Asn Glu Pro Tyr Arg Met Phe Thr Ser Arg Ala Glu Tyr
                420                 425                 430

Arg Leu Leu Leu Arg Glu Asp Asn Thr Leu Phe Arg Leu Gly Glu His
            435                 440                 445

Ala Tyr Arg Leu Gly Leu Met Glu Gln Asp Phe Tyr Lys Glu Leu Lys
        450                 455                 460

Lys Asp Lys Gln Glu Ile Gln Asp Asn Leu Lys Arg Leu Lys Glu Cys
465                 470                 475                 480

Val Leu Thr Pro Ser Lys Lys Leu Leu Lys Arg Leu Asn Glu Leu Asp
                485                 490                 495

Glu Asn Pro Ile Asn Asp Lys Val Asn Gly Val Ser Leu Leu Ala Arg
                500                 505                 510

Asp Ser Phe Asn Ala Glu Lys Met Arg Ser Phe Phe Ser Phe Leu Ala
            515                 520                 525

Pro Leu Asn Glu Arg Val Leu Glu Gln Ile Lys Ile Glu Cys Lys Tyr
        530                 535                 540

Asn Ile Tyr Ile Glu Lys Gln His Glu Asn Ile Ala Lys Met Asp Ser
545                 550                 555                 560

Met Leu Lys Val Ser Ile Pro Lys Gly Phe Val Phe Lys Gly Ile Pro
                565                 570                 575

Gly Leu Ser Leu Glu Ala Val Glu Lys Leu Glu Lys Phe Arg Pro Lys
                580                 585                 590

Ser Leu Phe Glu Ala Ser Glu Ile Ser Gly Ile Thr Pro Ala Asn Leu
            595                 600                 605

Asp Val Leu His Leu Tyr Ile His Leu Arg Lys Asn Ser
        610                 615                 620

<210> SEQ ID NO 3
<211> LENGTH: 1167
<212> TYPE: DNA
<213> ORGANISM: Artificial Sequence
<220> FEATURE:
<221> NAME/KEY: CDS
<222> LOCATION: (1)...(1164)
<223> OTHER INFORMATION: Description of Artificial Sequence:—ote =
      synthetic construct

<400> SEQUENCE: 3 atg aac gct tta gaa atc acc caa aag ctc atc agc tac ccc acc att      48
Met Asn Ala Leu Glu Ile Thr Gln Lys Leu Ile Ser Tyr Pro Thr Ile
 1               5                  10                  15 acg ccc aaa gaa tgc ggt att ttt gaa tac att aaa tcg ctt ttt cct      96
Thr Pro Lys Glu Cys Gly Ile Phe Glu Tyr Ile Lys Ser Leu Phe Pro
            20                  25                  30 gct ttt aaa aca cta gag tgt gga gaa aat ggc gtg aaa aac ctt ttt     144
Ala Phe Lys Thr Leu Glu Cys Gly Glu Asn Gly Val Lys Asn Leu Phe
        35                  40                  45 tta tac cgc att ttt aac ccc ccc aaa gag cat gca gaa aaa gaa cat     192
Leu Tyr Arg Ile Phe Asn Pro Pro Lys Glu His Ala Glu Lys Glu His
    50                  55                  60 gca aaa gaa aag cat gca aaa gaa aat gtt aag ccc ttg cat ttt tct     240
Ala Lys Glu Lys His Ala Lys Glu Asn Val Lys Pro Leu His Phe Ser
65                  70                  75                  80 ttt gca ggg cat att gat gtc gtg cct cct gga gat aat tgg caa agc     288
Phe Ala Gly His Ile Asp Val Val Pro Pro Gly Asp Asn Trp Gln Ser
```

```
                          85                  90                  95
gat ccc ttt aaa ccc atc att aaa gag ggg ttt tta tac ggc cgt ggg     336
Asp Pro Phe Lys Pro Ile Ile Lys Glu Gly Phe Leu Tyr Gly Arg Gly
            100                 105                 110 gcg caa gac atg aaa ggg ggc gtg ggg gcg ttt ttg agc gcg agt tta     384
Ala Gln Asp Met Lys Gly Gly Val Gly Ala Phe Leu Ser Ala Ser Leu
            115                 120                 125 aat ttt aac cct aaa acc cct ttt ttg ctt tct att tta ctc acg agc     432
Asn Phe Asn Pro Lys Thr Pro Phe Leu Leu Ser Ile Leu Leu Thr Ser
            130                 135                 140 gat gaa gaa ggg cca ggg att ttt ggc aca aaa ctc atg cta gaa aaa     480
Asp Glu Glu Gly Pro Gly Ile Phe Gly Thr Lys Leu Met Leu Glu Lys
145                 150                 155                 160 ctc aaa gaa aaa gat tta ttg ccc cat atg gcg att gtg gct gaa ccc     528
Leu Lys Glu Lys Asp Leu Leu Pro His Met Ala Ile Val Ala Glu Pro
            165                 170                 175 act tgc gaa aaa gtc tta ggc gat agc atc aaa att ggt cga aga ggt     576
Thr Cys Glu Lys Val Leu Gly Asp Ser Ile Lys Ile Gly Arg Arg Gly
            180                 185                 190 tcc att aat ggc aga ctc att tta aaa ggc gtt caa ggg cat gtg gct     624
Ser Ile Asn Gly Arg Leu Ile Leu Lys Gly Val Gln Gly His Val Ala
            195                 200                 205 tac cca caa aaa tgc caa aac ccc att gat acg ctc gct tct gtt ttg     672
Tyr Pro Gln Lys Cys Gln Asn Pro Ile Asp Thr Leu Ala Ser Val Leu
210                 215                 220 cct tca att tca gga gtc cat tta gac gat ggc gat gaa tat ttt gac     720
Pro Ser Ile Ser Gly Val His Leu Asp Asp Gly Asp Glu Tyr Phe Asp
225                 230                 235                 240 cct tca aaa ttg gtt gtc acc aac ttg cat gca ggg tta ggg gct aat     768
Pro Ser Lys Leu Val Val Thr Asn Leu His Ala Gly Leu Gly Ala Asn
            245                 250                 255 aat gtg act cca ggg agc gta gaa att acc ttt aat gcg cgc cat tct     816
Asn Val Thr Pro Gly Ser Val Glu Ile Thr Phe Asn Ala Arg His Ser
            260                 265                 270 tta aaa acc acc aaa gag agt ttg aaa gaa tat tta gaa aaa gtt tta     864
Leu Lys Thr Thr Lys Glu Ser Leu Lys Glu Tyr Leu Glu Lys Val Leu
            275                 280                 285 aaa gat ttg cct cac act tta gaa tta gag tca agc agt tcg cct ttc     912
Lys Asp Leu Pro His Thr Leu Glu Leu Glu Ser Ser Ser Ser Pro Phe
290                 295                 300 atc acg gct tct cat tca aag ctt acc agc gtt tta aaa gaa aat att     960
Ile Thr Ala Ser His Ser Lys Leu Thr Ser Val Leu Lys Glu Asn Ile
305                 310                 315                 320 tta aaa aca tgc cgc acc acc ccc ctt tta aac acc aaa ggc ggc acg    1008
Leu Lys Thr Cys Arg Thr Thr Pro Leu Leu Asn Thr Lys Gly Gly Thr
            325                 330                 335 agc gat gcg cga ttt ttt agc gct cat ggt ata gaa gtg gtg gag ttt    1056
Ser Asp Ala Arg Phe Phe Ser Ala His Gly Ile Glu Val Val Glu Phe
            340                 345                 350 ggc gtt att aat gac agg atc cat gcc att gat gaa agg gtg agc ttg    1104
Gly Val Ile Asn Asp Arg Ile His Ala Ile Asp Glu Arg Val Ser Leu
            355                 360                 365 aaa gaa tta gag ctt tta gaa aaa gtg ttt ttg ggg gtt tta gag ggc    1152
Lys Glu Leu Glu Leu Leu Glu Lys Val Phe Leu Gly Val Leu Glu Gly
            370                 375                 380 ttg agt gag gca taa                                                1167
Leu Ser Glu Ala
385
```

-continued

```
<210> SEQ ID NO 4
<211> LENGTH: 388
<212> TYPE: PRT
<213> ORGANISM: Artificial Sequence
<220> FEATURE:
<223> OTHER INFORMATION: Description of Artificial Sequence:—ote =
      synthetic construct

<400> SEQUENCE: 4

Met Asn Ala Leu Glu Ile Thr Gln Lys Leu Ile Ser Tyr Pro Thr Ile
 1               5                  10                  15

Thr Pro Lys Glu Cys Gly Ile Phe Glu Tyr Ile Lys Ser Leu Phe Pro
            20                  25                  30

Ala Phe Lys Thr Leu Glu Cys Gly Glu Asn Gly Val Lys Asn Leu Phe
        35                  40                  45

Leu Tyr Arg Ile Phe Asn Pro Pro Lys Glu His Ala Glu Lys Glu His
 50                  55                  60

Ala Lys Glu Lys His Ala Lys Glu Asn Val Lys Pro Leu His Phe Ser
65                  70                  75                  80

Phe Ala Gly His Ile Asp Val Val Pro Pro Gly Asp Asn Trp Gln Ser
                85                  90                  95

Asp Pro Phe Lys Pro Ile Ile Lys Glu Gly Phe Leu Tyr Gly Arg Gly
            100                 105                 110

Ala Gln Asp Met Lys Gly Gly Val Gly Ala Phe Leu Ser Ala Ser Leu
        115                 120                 125

Asn Phe Asn Pro Lys Thr Pro Phe Leu Leu Ser Ile Leu Leu Thr Ser
    130                 135                 140

Asp Glu Glu Gly Pro Gly Ile Phe Gly Thr Lys Leu Met Leu Glu Lys
145                 150                 155                 160

Leu Lys Glu Lys Asp Leu Leu Pro His Met Ala Ile Val Ala Glu Pro
                165                 170                 175

Thr Cys Glu Lys Val Leu Gly Asp Ser Ile Lys Ile Gly Arg Arg Gly
            180                 185                 190

Ser Ile Asn Gly Arg Leu Ile Leu Lys Gly Val Gln Gly His Val Ala
        195                 200                 205

Tyr Pro Gln Lys Cys Gln Asn Pro Ile Asp Thr Leu Ala Ser Val Leu
    210                 215                 220

Pro Ser Ile Ser Gly Val His Leu Asp Asp Gly Asp Glu Tyr Phe Asp
225                 230                 235                 240

Pro Ser Lys Leu Val Val Thr Asn Leu His Ala Gly Leu Gly Ala Asn
                245                 250                 255

Asn Val Thr Pro Gly Ser Val Glu Ile Thr Phe Asn Ala Arg His Ser
            260                 265                 270

Leu Lys Thr Thr Lys Glu Ser Leu Lys Glu Tyr Leu Glu Lys Val Leu
        275                 280                 285

Lys Asp Leu Pro His Thr Leu Glu Leu Glu Ser Ser Ser Pro Phe
    290                 295                 300

Ile Thr Ala Ser His Ser Lys Leu Thr Ser Val Leu Lys Glu Asn Ile
305                 310                 315                 320

Leu Lys Thr Cys Arg Thr Thr Pro Leu Leu Asn Thr Lys Gly Gly Thr
                325                 330                 335

Ser Asp Ala Arg Phe Phe Ser Ala His Gly Ile Glu Val Val Glu Phe
            340                 345                 350

Gly Val Ile Asn Asp Arg Ile His Ala Ile Asp Glu Arg Val Ser Leu
        355                 360                 365
```

```
Lys Glu Leu Glu Leu Leu Glu Lys Val Phe Leu Gly Val Leu Glu Gly
    370                 375                 380

Leu Ser Glu Ala
385

<210> SEQ ID NO 5
<211> LENGTH: 753
<212> TYPE: DNA
<213> ORGANISM: Artificial Sequence
<220> FEATURE:
<221> NAME/KEY: CDS
<222> LOCATION: (1)...(750)
<223> OTHER INFORMATION: Description of Artificial Sequence:—ote =
      synthetic construct

<400> SEQUENCE: 5 atg cta gga agc gtt aaa aaa acc ttt ttt tgg gtc ttg tgt ttg ggc       48
Met Leu Gly Ser Val Lys Lys Thr Phe Phe Trp Val Leu Cys Leu Gly
1               5                   10                  15 gcg ttg tgt tta aga ggg tta atg gca gag cca gac gct aaa gag ctt       96
Ala Leu Cys Leu Arg Gly Leu Met Ala Glu Pro Asp Ala Lys Glu Leu
                20                  25                  30 gtt aat tta ggc ata gag agc gcg aag aag caa gat ttc gct caa gct      144
Val Asn Leu Gly Ile Glu Ser Ala Lys Lys Gln Asp Phe Ala Gln Ala
        35                  40                  45 aaa acg cat ttt gaa aaa gct tgt gag tta aaa aat ggc ttt ggg tgt      192
Lys Thr His Phe Glu Lys Ala Cys Glu Leu Lys Asn Gly Phe Gly Cys
50                  55                  60 gtt ttt tta ggg gcg ttc tat gaa gaa ggg aaa gga gtg gga aaa gac      240
Val Phe Leu Gly Ala Phe Tyr Glu Glu Gly Lys Gly Val Gly Lys Asp
65                  70                  75                  80 ttg aaa aaa gcc atc cag ttt tac act aaa agt tgt gaa tta aat gat      288
Leu Lys Lys Ala Ile Gln Phe Tyr Thr Lys Ser Cys Glu Leu Asn Asp
                85                  90                  95 ggt tat ggg tgc aac ctg cta gga aat tta tac tat aac gga caa ggc      336
Gly Tyr Gly Cys Asn Leu Leu Gly Asn Leu Tyr Tyr Asn Gly Gln Gly
            100                 105                 110 gta tct aaa gac gct aaa aaa gcc tca caa tac tac tct aaa gct tgc      384
Val Ser Lys Asp Ala Lys Lys Ala Ser Gln Tyr Tyr Ser Lys Ala Cys
        115                 120                 125 gac tta aac cat gct gaa ggg tgt atg gta tta gga agc tta cac cat      432
Asp Leu Asn His Ala Glu Gly Cys Met Val Leu Gly Ser Leu His His
130                 135                 140 tat ggc gta ggc acg cct aag gat tta aga aag gct ctt gat ttg tat      480
Tyr Gly Val Gly Thr Pro Lys Asp Leu Arg Lys Ala Leu Asp Leu Tyr
145                 150                 155                 160 gaa aaa gct tgc gat tta aaa gac agc cca ggg tgt att aat gca gga      528
Glu Lys Ala Cys Asp Leu Lys Asp Ser Pro Gly Cys Ile Asn Ala Gly
                165                 170                 175 tat ata tat agt gta aca aag aat ttt aag gag gct atc gtt cgt tat      576
Tyr Ile Tyr Ser Val Thr Lys Asn Phe Lys Glu Ala Ile Val Arg Tyr
            180                 185                 190 tct caa gca tgc gag ttg aac gat ggt agg ggg tgt tat aat tta ggg      624
Ser Gln Ala Cys Glu Leu Asn Asp Gly Arg Gly Cys Tyr Asn Leu Gly
        195                 200                 205 gtt atg caa tac aac gct caa ggc aca gca aaa gac gaa aag caa gcg      672
Val Met Gln Tyr Asn Ala Gln Gly Thr Ala Lys Asp Glu Lys Gln Ala
    210                 215                 220 gta gaa aac ttt aaa aaa ggt tgc aaa tca ggc gtt aaa gaa gca tgc      720
Val Glu Asn Phe Lys Lys Gly Cys Lys Ser Gly Val Lys Glu Ala Cys
225                 230                 235                 240
```

```
gac gct ctc aag gaa ttg aaa ata gaa ctt tag                         753
Asp Ala Leu Lys Glu Leu Lys Ile Glu Leu
                245                 250
```

<210> SEQ ID NO 6
<211> LENGTH: 250
<212> TYPE: PRT
<213> ORGANISM: Artificial Sequence
<220> FEATURE:
<223> OTHER INFORMATION: Description of Artificial Sequence:—ote = synthetic construct

<400> SEQUENCE: 6

```
Met Leu Gly Ser Val Lys Lys Thr Phe Phe Trp Val Leu Cys Leu Gly
 1               5                  10                  15

Ala Leu Cys Leu Arg Gly Leu Met Ala Glu Pro Asp Ala Lys Glu Leu
                20                  25                  30

Val Asn Leu Gly Ile Glu Ser Ala Lys Lys Gln Asp Phe Ala Gln Ala
            35                  40                  45

Lys Thr His Phe Glu Lys Ala Cys Glu Leu Lys Asn Gly Phe Gly Cys
50                  55                  60

Val Phe Leu Gly Ala Phe Tyr Glu Glu Gly Lys Gly Val Gly Lys Asp
65                  70                  75                  80

Leu Lys Lys Ala Ile Gln Phe Tyr Thr Lys Ser Cys Glu Leu Asn Asp
                85                  90                  95

Gly Tyr Gly Cys Asn Leu Leu Gly Asn Leu Tyr Tyr Asn Gly Gln Gly
            100                 105                 110

Val Ser Lys Asp Ala Lys Lys Ala Ser Gln Tyr Tyr Ser Lys Ala Cys
        115                 120                 125

Asp Leu Asn His Ala Glu Gly Cys Met Val Leu Gly Ser Leu His His
    130                 135                 140

Tyr Gly Val Gly Thr Pro Lys Asp Leu Arg Lys Ala Leu Asp Leu Tyr
145                 150                 155                 160

Glu Lys Ala Cys Asp Leu Lys Asp Ser Pro Gly Cys Ile Asn Ala Gly
                165                 170                 175

Tyr Ile Tyr Ser Val Thr Lys Asn Phe Lys Glu Ala Ile Val Arg Tyr
            180                 185                 190

Ser Gln Ala Cys Glu Leu Asn Asp Gly Arg Gly Cys Tyr Asn Leu Gly
        195                 200                 205

Val Met Gln Tyr Asn Ala Gln Gly Thr Ala Lys Asp Glu Lys Gln Ala
    210                 215                 220

Val Glu Asn Phe Lys Lys Gly Cys Lys Ser Gly Val Lys Glu Ala Cys
225                 230                 235                 240

Asp Ala Leu Lys Glu Leu Lys Ile Glu Leu
                245                 250
```

<210> SEQ ID NO 7
<211> LENGTH: 5049
<212> TYPE: DNA
<213> ORGANISM: Artificial Sequence
<220> FEATURE:
<223> OTHER INFORMATION: Description of Artificial Sequence:—ote = synthetic construct

<400> SEQUENCE: 7

```
aattccctat catgaaacct aaaatcaatc tcctagggct tgtgcctact agtaaataat    60
gcttaaagcg atgcgcgtgt gcaaattcca tttttgcatg cttaaagcta aaataaaccc   120
tcccataaaa agaaagataa tcggcgatgc gtaagaagag ctgacgctag cgaattgatc   180
```

-continued

```
cacgctaaag acgctaaaaa gcaccaaagg taaaagcgcg gttgcaggca ggtcaatggt      240
ttctgtcatc caccatatcc ccattaaaac agccacccca gccacaacag gcatcgcctt      300
ataatttaag gaattaagct tggggatttc ttctacaata tgaggcagtt gagaattgag      360
cgcataacag ataataagcg cgattaacac tcctcctatt aaccccaaca agtgcacgat      420
cttagtgctt ttatcatcgg tgcgcgtatc ggtatgcgta ttggcatgcg aatgattttc      480
cattttattt tacccttcaa aattactaac ctccatgcta caataaaacg ttttcaaaac      540
taagatttta gaaaaatcat atcaaaacag gaaaagagt ggtaaaagaa agtgatattt      600
tagtgattgg tgggggggcat gcgggcattg aagcgagctt gattgcagcc aaaatggggg      660
ctagggtgca tttaatcacc atgctcatag acacgatcgg tttagcgagc tgtaacccgg      720
cgattggggg cttgggtaaa gggcatttga ctaagaagt ggatgtttta gggggggcta      780
tgggattat tacagatcat agcggtttgc aatatcgtgt gttaaacgct tctaaagggc      840
cggcggttag ggggactaga gcgcaaattg atatggatac ttaccgcatt tttgcaagaa      900
atcttgtttt aaacacccct aatttgagcg tctctcaaga aatgaccgaa agtttaatcc      960
ttgaaaacga tgaggtagtg ggcgtaacca cgaacattaa taacacttac agagctaaaa     1020
aagtgatcat caccacaggc actttttaa aaggggtggt gcatattggc gagcaccaaa     1080
accaaaacgg gcgttttggg gaaaacgctt ccaattcttt agccttgaat ttaagggagc     1140
ttggctttaa ggtggagagg ttaaaaaccg gcacttgccc aagagtggcc ggcaatagca     1200
ttgattttga aggcttagaa gagcattttg gggatgcaaa ccctccctat ttcagctata     1260
aaaccaaaga ttttaacccc acccaactct cttgtttcat cacttacact aaccccatta     1320
cccaccaaat cattagggat aatttccacc gagctcccct ttttagcggt caaattgaag     1380
gcataggccc aagtattgc cctagcattg aagataaaat caaccgcttt agtgaaaaag     1440
aacgccacca gctgttttta gagcctcaaa ccattcataa aaacgaatat tatatcaacg     1500
gcttaagcac ctctttgccc ctagatgtgc aagaaaaggt cattcattct atcaaaggct     1560
tagaaaacgc cctcatcacg cgctatggct atgcgataga gtatgatttc atccagccta     1620
cagaattaac ccacgcttta gaaaccaaaa aaatcaaagg gctttatttg gccgggcaaa     1680
tcaatgggac taccggctat gaagaagcgg cggatcaagg gcttatggct gggattaatg     1740
cggtattagc cttaaagaat caagcccct ttatttaaa gcgcaatgaa gcttatattg     1800
gcgttttgat tgatgatttg gttactaaag gcacgaatga gccttacaga atgtttacta     1860
gccgagccga ataccgcttg cttttaagag aggacaacac gcttttagg ttgggcgaac     1920
atgcctatcg tttagggctt atggaacagg atttttataa ggaattaaaa aaagataaac     1980
aagagataca agacaatctc aaacgcctta agaatgcgt ccttacccct agtaaaaaat     2040
tgttaaaacg cttgaacgaa ttagacgaaa accctatcaa tgacaaggtt aatggcgtta     2100
gtttgttagc acgcgatagt tttaatgcag aaaaaatgcg ctccttttc agcttttag     2160
cccccttgaa cgagcgggtt ttagagcaga ttaaaattga atgcaaatat aatatttata     2220
ttgaaaagca acacgaaaat atcgctaaaa tggatagcat gctcaaagtt tctatcccta     2280
aaggttttgt gttaaaggc attccaggct taagcttaga agcggtagaa aaattagaaa     2340
aattccgccc caaagcctt tttgaagcct cagaaatcag cgggatcact ccagcgaatt     2400
tagacgtttt gcatttatac atccatttgc gaaaaaactc ttaaaggatt tttaatgaac     2460
gctttagaaa tcacccaaaa gctcatcagc taccccacca ttacgcccaa agaatgcggt     2520
```

```
atttttgaat acattaaatc gcttttcct gcttttaaaa cactagagtg tggagaaaat      2580
ggcgtgaaaa accttttttt ataccgcatt tttaaccccc ccaaagagca tgcagaaaaa      2640
gaacatgcaa aagaaaagca tgcaaaagaa aatgttaagc ccttgcattt ttcttttgca      2700
gggcatattg atgtcgtgcc tcctggagat aattggcaaa gcgatccctt taaacccatc      2760
attaaagagg ggtttttata cggccgtggg gcgcaagaca tgaaagggggg cgtgggggcg      2820
tttttgagcg cgagtttaaa ttttaaccct aaaacccctt ttttgctttc tattttactc      2880
acgagcgatg aagaagggcc agggattttt ggcacaaaac tcatgctaga aaaactcaaa      2940
gaaaaagatt tattgcccca tatggcgatt gtggctgaac ccacttgcga aaaagtctta      3000
ggcgatagca tcaaaattgg tcgaagaggt tccattaatg gcagactcat tttaaaaggc      3060
gttcaagggc atgtggctta cccacaaaaa tgccaaaacc ccattgatac gctcgcttct      3120
gttttgcctt caatttcagg agtccattta gacgatggcg atgaatattt tgacccttca      3180
aaattggttg tcaccaactt gcatgcaggg ttagggcta ataatgtgac tccagggagc      3240
gtagaaatta cctttaatgc gcgccattct ttaaaaacca ccaaagagag tttgaaagaa      3300
tatttagaaa aagtttttaaa agatttgcct cacactttag aattagagtc aagcagttcg      3360
cctttcatca cggcttctca ttcaaagctt accagcgttt taaaagaaaa tattttaaaa      3420
acatgccgca ccacccccct tttaaacacc aaaggcggca cgagcgatgc gcgattttt      3480
agcgctcatg gtatagaagt ggtggagttt ggcgttatta atgacaggat ccatgccatt      3540
gatgaaaggg tgagcttgaa agaattagag cttttagaaa aagtgttttt ggggttttta      3600
gagggcttga gtgaggcata aaataaataa acattaagta aggcttatca atatttgatt      3660
acaattataa agggttacat ttttttaata ggagatatac catgctagga agcgttaaaa      3720
aaacctttt ttgggtcttg tgtttgggcg cgttgtgttt aagagggtta atggcagagc      3780
cagacgctaa agagcttgtt aatttaggca tagagagcgc gaagaagcaa gatttcgctc      3840
aagctaaaac gcattttgaa aaagcttgtg agttaaaaaa tggctttggg tgtgttttt      3900
tagggcgtt ctatgaagaa gggaaaggag tgggaaaaga cttgaaaaaa gccatccagt      3960
tttacactaa aagttgtgaa ttaaatgatg gttatgggtg caacctgcta ggaaatttat      4020
actataacgg acaaggcgta tctaaagacg ctaaaaaagc ctcacaatac tactctaaag      4080
cttgcgactt aaaccatgct gaagggtgta tggtattagg aagcttacac cattatggcg      4140
taggcacgcc taaggattta agaaaggctc ttgatttgta tgaaaaagct tgcgatttaa      4200
aagacagccc aggtgtatt aatgcaggat atatatatag tgtaacaaag aattttaagg      4260
aggctatcgt tcgttattct caagcatgcg agttgaacga tggtaggggg tgttataatt      4320
tagggggttat gcaatacaac gctcaaggca cagcaaaaga cgaaaagcaa gcggtagaaa      4380
actttaaaaa aggttgcaaa tcaggcgtta aagaagcatg cgacgctctc aaggaattga      4440
aaatagaact ttagtttcaa taaagttaag ccaaacgccg tgtttagctg gcttctacgc      4500
ttttaatat cttaatgaaa gcataaaccc tacaaactaa tcttttaatc ataataaggg      4560
ttttatatcg cacccattca ttgccgtttt tagattggcg cttgaaaggt ttaaagcaag      4620
tttgttcaaa ccccttaaaaa gggtttttaa ccccctacaac gctttcaata gcacgctatt      4680
taggcgttcg gtaaaacttt tagcgtcttt taaagcccct ttttctaaaa gcttcgcccc      4740
atcataaagc aaccagataa aagcgttcaa ctgctcttta tcttcgcatt ttaagagttt      4800
ttggaaaatc gcatggttag ggtttaattc tagcgttttc ttgctttcag gcacgctttg      4860
acccatttga cgcataaaat tagccatcat cgcattttgg tcatcgccta ttaaagccac      4920
```

```
cgctgaagtg agatgactgg aaagctctac gcctttaatc tcatctttaa gattttcttc    4980
aaacgctttc attaaatctt taaactgatc ttttatctca tcaaggattt cttccaaacc    5040
aagggttaa                                                            5049
```

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 8

```
caggaaaaag agtggtaa                                                    18
```

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 9

```
ttaagagttt tttcgcaa                                                    18
```

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 10

```
aaggatattt aatgaacg                                                    18
```

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 11

```
gtttatttat tttatgcctc a                                                21
```

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 12

```
taatttaggc atagagagc                                                   19
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:—ote = synthetic construct

<400> SEQUENCE: 13
tataacggac aaggcgtatc t                                              21

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 14
gttctatttt caattccttg agag                                           24

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 15
gcgtgaatga atacgata                                                  18

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 16
ctcccaccag cttatatacc ttag                                           24

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 17
ctggggatca agcctgattg g                                              21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 18
gaccgttccg tggcaaagca                                                20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 19
cttgtgcaat gtaacatcag ag                                        22

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 20
gcattccagg cttaagct                                             18

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 21
tgcatgttct ttttctgcat                                           20

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 22
gagtttggcg ttattaat                                             18

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 23 gcttttcaa aatgcgt                                              17

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence:—ote =
      synthetic construct

<400> SEQUENCE: 24
aagcttgatc actcc                                                15

<210> SEQ ID NO 25
<211> LENGTH: 613
<212> TYPE: PRT
<213> ORGANISM: H. influenzae

<400> SEQUENCE: 25

Met Phe Tyr Thr Glu Thr Tyr Asp Val Ile Val Ile Gly Gly Gly His

-continued

```
  1               5                  10                 15
Ala Gly Thr Glu Ala Ala Leu Ala Pro Ala Arg Met Gly Phe Lys Thr
             20              25              30
Leu Leu Leu Thr His Asn Val Asp Thr Leu Gly Gln Met Ser Cys Asn
         35              40              45
Pro Ala Ile Gly Gly Ile Gly Lys Gly His Leu Val Lys Glu Val Asp
 50              55              60
Ala Met Gly Gly Leu Met Ala His Ala Ala Asp Lys Ala Gly Ile Gln
 65              70              75              80
Phe Arg Thr Leu Asn Ser Ser Lys Gly Pro Ala Val Arg Ala Thr Arg
             85              90              95
Ala Gln Ser Asp Arg Val Leu Tyr Arg Gln Ala Val Arg Thr Ala Leu
            100             105             110
Glu Asn Gln Pro Asn Leu Asp Ile Phe Gln Gln Glu Ala Thr Asp Ile
            115             120             125
Leu Ile Glu Gln Asp Arg Val Thr Gly Val Ser Thr Lys Met Gly Leu
130             135             140
Thr Phe Arg Ala Lys Ser Val Ile Leu Thr Ala Gly Thr Phe Leu Ala
145             150             155             160
Gly Lys Ile His Ile Gly Leu Glu Asn Tyr Glu Gly Arg Ala Gly
            165             170             175
Asp Ser Ala Ser Val Asn Leu Ser His Arg Leu Arg Asp Leu Gly Leu
            180             185             190
Arg Val Asp Arg Leu Lys Thr Gly Thr Pro Arg Ile Asp Ala Arg
            195             200             205
Thr Ile Asn Phe Asp Ile Leu Ala Lys Gln His Gly Asp Glu Val Leu
            210             215             220
Pro Val Phe Ser Phe Met Gly Ser Val Asp Asp His Pro Gln Gln Ile
225             230             235             240
Pro Cys Tyr Ile Thr His Thr Asn Glu Gln Thr His Glu Val Ile Arg
            245             250             255
Asn Asn Leu Asp Arg Ser Pro Met Tyr Thr Gly Val Ile Glu Gly Ile
            260             265             270
Gly Pro Arg Tyr Cys Pro Ser Ile Glu Asp Lys Val Met Arg Phe Ala
            275             280             285
Asp Arg Asn Ser His Gln Ile Tyr Leu Glu Pro Glu Gly Leu Thr Ser
290             295             300
Asn Glu Val Tyr Pro Asn Gly Ile Ser Thr Ser Leu Pro Phe Asp Val
305             310             315             320
Gln Met Gly Ile Val Asn Ser Met Lys Gly Leu Glu Asn Ala Arg Ile
            325             330             335
Val Lys Pro Gly Tyr Ala Ile Glu Tyr Asp Tyr Phe Asp Pro Arg Asp
            340             345             350
Leu Lys Pro Thr Leu Glu Thr Lys Ser Ile Ser Gly Leu Phe Phe Ala
            355             360             365
Gly Gln Ile Asn Gly Thr Thr Gly Tyr Glu Glu Ala Ala Gln Gly
            370             375             380
Leu Leu Ala Gly Ile Asn Ala Gly Leu Tyr Val Gln Glu Lys Asp Ala
385             390             395             400
Trp Tyr Pro Arg Arg Asp Gln Ser Tyr Thr Gly Val Leu Val Asp Asp
            405             410             415
Leu Cys Thr Leu Gly Thr Lys Glu Pro Tyr Arg Val Phe Thr Ser Arg
            420             425             430
```

-continued

```
Ala Glu Tyr Arg Leu Leu Arg Glu Asp Asn Ala Asp Ile Arg Leu
            435                 440                 445

Thr Pro Ile Ala His Glu Leu Gly Leu Ile Asp Glu Ala Arg Trp Ala
    450                 455                 460

Arg Phe Asn Gln Lys Met Glu Asn Ile Glu Gln Glu Arg Gln Arg Leu
465                 470                 475                 480

Arg Ser Ile Trp Leu His Pro Arg Ser Glu Tyr Leu Glu Glu Ala Asn
                485                 490                 495

Lys Val Leu Gly Ser Pro Leu Val Arg Glu Ala Ser Gly Glu Asp Leu
                500                 505                 510

Leu Arg Arg Pro Glu Met Thr Tyr Asp Ile Leu Thr Ser Leu Thr Pro
            515                 520                 525

Tyr Lys Pro Ala Met Glu Asp Lys Glu Ala Val Glu Gln Val Glu Ile
        530                 535                 540

Ala Ile Lys Tyr Gln Gly Tyr Ile Glu His Gln Asn Phe Asp Tyr
545                 550                 555                 560

Ser Lys Val Ser Gly Leu Ser Asn Glu Val Arg Ala Lys Leu Glu Gln
                565                 570                 575

His Arg Pro Val Ser Ile Gly Gln Ala Ser Arg Ile Ser Gly Ile Thr
            580                 585                 590

Pro Ala Ala Ile Ser Ile Ile Leu Val Asn Leu Lys Lys Gln Gly Met
        595                 600                 605

Leu Lys Arg Gly Glu
        610
```

<210> SEQ ID NO 26
<211> LENGTH: 621
<212> TYPE: PRT
<213> ORGANISM: H. pylori

<400> SEQUENCE: 26

```
Met Val Lys Glu Ser Asp Ile Leu Val Ile Gly Gly His Ala Gly
1               5                   10                  15

Ile Glu Ala Ser Leu Ile Ala Ala Lys Met Gly Ala Arg Val His Leu
                20                  25                  30

Ile Thr Met Leu Ile Asp Thr Ile Gly Leu Ala Ser Cys Asn Pro Ala
            35                  40                  45

Ile Gly Gly Leu Gly Lys Gly His Leu Thr Lys Glu Val Asp Val Leu
        50                  55                  60

Gly Gly Ala Met Gly Ile Ile Thr Asp His Ser Gly Leu Gln Tyr Arg
65                  70                  75                  80

Val Leu Asn Ala Ser Lys Gly Pro Ala Val Arg Gly Thr Arg Ala Gln
                85                  90                  95

Ile Asp Met Asp Thr Tyr Arg Ile Phe Ala Arg Asn Leu Val Leu Asn
            100                 105                 110

Thr Pro Asn Leu Ser Val Ser Gln Glu Met Thr Glu Ser Leu Ile Leu
        115                 120                 125

Glu Asn Asp Glu Val Val Gly Val Thr Thr Asn Ile Asn Asn Thr Tyr
    130                 135                 140

Arg Ala Lys Lys Val Ile Ile Thr Thr Gly Thr Phe Leu Lys Gly Val
145                 150                 155                 160

Val His Ile Gly Glu His Gln Asn Gln Asn Gly Arg Phe Gly Glu Asn
                165                 170                 175

Ala Ser Asn Ser Leu Ala Ile Asn Leu Arg Glu Leu Gly Phe Lys Val
```

-continued

```
                180                 185                 190
Glu Arg Leu Lys Thr Gly Thr Cys Pro Arg Val Ala Gly Asn Ser Ile
            195                 200                 205
Asp Phe Glu Gly Leu Glu His Phe Gly Asp Ala Asn Pro Pro Tyr
210                 215                 220
Phe Ser Tyr Lys Thr Lys Asp Phe Asn Pro Thr Gln Leu Ser Cys Phe
225                 230                 235                 240
Ile Thr Tyr Thr Asn Pro Ile Thr His Gln Ile Ile Arg Asp Asn Phe
                245                 250                 255
His Arg Ala Pro Leu Phe Ser Gly Gln Ile Glu Gly Ile Gly Pro Arg
                260                 265                 270
Tyr Cys Pro Ser Ile Glu Asp Lys Ile Asn Arg Phe Ser Glu Lys Glu
            275                 280                 285
Arg His Gln Leu Phe Leu Glu Pro Gln Thr Ile His Lys Asn Glu Tyr
            290                 295                 300
Tyr Ile Asn Gly Leu Ser Thr Ser Leu Pro Leu Asp Val Gln Glu Lys
305                 310                 315                 320
Val Ile His Ser Ile Lys Gly Leu Glu Asn Ala Leu Ile Thr Arg Tyr
                325                 330                 335
Gly Tyr Ala Ile Glu Tyr Asp Phe Ile Gln Pro Thr Glu Leu Thr His
                340                 345                 350
Ala Leu Glu Thr Lys Lys Ile Lys Gly Leu Tyr Leu Ala Gly Gln Ile
            355                 360                 365
Asn Gly Thr Thr Gly Tyr Glu Glu Ala Ala Asp Gln Gly Leu Met Ala
            370                 375                 380
Gly Ile Asn Ala Val Leu Ala Leu Lys Asn Gln Ala Pro Phe Ile Leu
385                 390                 395                 400
Lys Arg Asn Glu Ala Tyr Ile Gly Val Leu Ile Asp Asp Leu Val Thr
                405                 410                 415
Lys Gly Thr Asn Glu Pro Tyr Arg Met Phe Thr Ser Arg Ala Glu Tyr
                420                 425                 430
Arg Leu Leu Leu Arg Glu Asp Asn Thr Leu Phe Arg Leu Gly Glu His
            435                 440                 445
Ala Tyr Arg Leu Gly Leu Met Glu Gln Asp Phe Tyr Lys Glu Leu Lys
            450                 455                 460
Lys Asp Lys Gln Glu Ile Gln Asp Asn Leu Lys Arg Leu Lys Glu Cys
465                 470                 475                 480
Val Leu Thr Pro Ser Lys Leu Leu Lys Arg Leu Asn Glu Leu Asp
                485                 490                 495
Glu Asn Pro Ile Asn Asp Lys Val Asn Gly Val Ser Leu Leu Ala Arg
                500                 505                 510
Asp Ser Phe Asn Ala Glu Lys Met Arg Ser Phe Ser Phe Leu Ala
            515                 520                 525
Pro Leu Asn Glu Arg Val Leu Glu Gln Ile Lys Ile Glu Cys Lys Tyr
            530                 535                 540
Asn Ile Tyr Ile Glu Lys Gln His Glu Asn Ile Ala Lys Met Asp Ser
545                 550                 555                 560
Met Leu Lys Val Ser Ile Pro Lys Gly Phe Val Phe Lys Gly Ile Pro
                565                 570                 575
Gly Leu Ser Leu Glu Ala Val Glu Lys Leu Glu Lys Phe Arg Pro Lys
            580                 585                 590
Ser Leu Phe Glu Ala Ser Glu Ile Ser Gly Ile Thr Pro Ala Asn Leu
            595                 600                 605
```

-continued

Asp Val Leu His Leu Tyr Ile His Leu Arg Lys Asn Ser
    610                 615                 620

<210> SEQ ID NO 27
<211> LENGTH: 626
<212> TYPE: PRT
<213> ORGANISM: E. coli

<400> SEQUENCE: 27

Met Phe Tyr Pro Asp Pro Phe Asp Val Ile Ile Gly Gly His
1               5                   10                  15

Ala Gly Thr Glu Ala Ala Met Ala Ala Arg Met Gly Gln Gln Thr
            20                  25                  30

Leu Leu Leu Thr His Asn Ile Asp Thr Leu Gly Gln Met Ser Cys Asn
        35                  40                  45

Pro Ala Ile Gly Gly Ile Gly Lys Gly His Leu Val Lys Glu Val Asp
    50                  55                  60

Ala Leu Gly Gly Leu Met Ala Lys Ala Ile Asp Gln Ala Gly Ile Gln
65                  70                  75                  80

Phe Arg Ile Leu Asn Ala Ser Lys Gly Pro Ala Val Arg Ala Thr Arg
                85                  90                  95

Ala Gln Ala Asp Arg Val Leu Tyr Arg Gln Ala Val Arg Thr Ala Leu
            100                 105                 110

Glu Asn Gln Pro Asn Leu Met Ile Phe Gln Gln Ala Val Glu Asp Leu
        115                 120                 125

Ile Val Glu Asn Asp Arg Val Val Gly Ala Val Thr Gln Met Gly Leu
    130                 135                 140

Lys Phe Arg Ala Lys Ala Val Val Leu Thr Val Gly Thr Phe Leu Asp
145                 150                 155                 160

Gly Lys Ile His Ile Gly Leu Asp Asn Tyr Ser Gly Gly Arg Ala Gly
                165                 170                 175

Asp Pro Pro Ser Ile Pro Leu Ser Arg Arg Leu Arg Glu Leu Pro Leu
            180                 185                 190

Arg Val Gly Arg Leu Lys Thr Gly Thr Pro Pro Arg Ile Asp Ala Arg
        195                 200                 205

Thr Ile Asp Phe Ser Val Leu Ala Gln Gln His Gly Asp Asn Pro Met
    210                 215                 220

Pro Val Phe Ser Phe Met Gly Asn Ala Ser Gln His Pro Gln Gln Val
225                 230                 235                 240

Pro Cys Tyr Ile Thr His Thr Asn Glu Lys Thr His Asp Val Ile Arg
                245                 250                 255

Ser Asn Leu Asp Arg Ser Pro Met Tyr Ala Gly Val Ile Glu Gly Val
            260                 265                 270

Gly Pro Arg Tyr Cys Pro Ser Ile Glu Asp Lys Val Met Arg Phe Ala
        275                 280                 285

Asp Arg Asn Gln His Gln Ile Phe Leu Glu Pro Glu Gly Leu Thr Ser
    290                 295                 300

Asn Glu Ile Tyr Pro Asn Gly Ile Ser Thr Ser Leu Pro Phe Asp Val
305                 310                 315                 320

Gln Met Gln Ile Val Arg Ser Met Gln Gly Met Glu Asn Ala Lys Ile
                325                 330                 335

Val Arg Pro Gly Tyr Ala Ile Glu Tyr Asp Phe Phe Asp Pro Arg Asp
            340                 345                 350

Leu Lys Pro Thr Leu Glu Ser Lys Phe Ile Gln Gly Leu Phe Phe Ala

-continued

```
                355                 360                 365
Gly Gln Ile Asn Gly Thr Thr Gly Tyr Glu Glu Ala Ala Gln Gly
            370                 375                 380
Leu Leu Ala Gly Leu Asn Ala Ala Arg Leu Ser Ala Asp Lys Glu Gly
385                 390                 395                 400
Trp Ala Pro Ala Arg Ser Gln Ala Tyr Leu Gly Val Leu Val Asp Asp
                405                 410                 415
Leu Cys Thr Leu Gly Thr Lys Glu Pro Tyr Arg Met Phe Thr Ser Arg
                420                 425                 430
Ala Glu Tyr Arg Leu Met Leu Arg Glu Asp Asn Ala Asp Leu Arg Leu
                435                 440                 445
Thr Glu Ile Gly Arg Glu Leu Gly Leu Val Asp Asp Glu Arg Trp Ala
            450                 455                 460
Arg Phe Asn Glu Lys Leu Glu Asn Ile Glu Arg Glu Arg Gln Arg Leu
465                 470                 475                 480
Lys Ser Thr Trp Val Thr Pro Ser Ala Glu Ala Ala Glu Val Asn
                485                 490                 495
Ala His Leu Thr Ala Pro Leu Ser Arg Glu Ala Ser Gly Glu Asp Leu
            500                 505                 510
Leu Arg Pro Glu Met Thr Tyr Glu Lys Leu Thr Thr Leu Thr Pro Phe
            515                 520                 525
Ala Pro Ala Leu Thr Asp Glu Gln Ala Ala Glu Gln Val Glu Ile Gln
            530                 535                 540
Val Lys Tyr Glu Gly Tyr Ile Ala Arg Gln Gln Asp Glu Ile Glu Lys
545                 550                 555                 560
Gln Leu Arg Asn Glu Asn Thr Leu Leu Pro Ala Thr Leu Asp Tyr Arg
                565                 570                 575
Gln Val Ser Gly Leu Ser Asn Glu Val Ile Ala Lys Leu Asn Asp His
            580                 585                 590
Lys Pro Ala Ser Ile Gly Gln Ala Ser Arg Ile Ser Gly Val Thr Pro
            595                 600                 605
Ala Ala Ile Ser Ile Leu Leu Val Trp Leu Lys Lys Gln Gly Met Leu
        610                 615                 620
Arg Arg
625

<210> SEQ ID NO 28
<211> LENGTH: 355
<212> TYPE: PRT
<213> ORGANISM: H. influenzae

<400> SEQUENCE: 28

Met Lys Glu Lys Val Val Ser Leu Ala Gln Asp Leu Ile Arg Arg Pro
  1                 5                  10                  15
Ser Ile Ser Pro Asn Asp Glu Gly Cys Gln Gln Ile Ile Ala Glu Arg
                20                  25                  30
Leu Glu Lys Leu Gly Phe Gln Ile Glu Trp Met Pro Phe Asn Asp Thr
            35                  40                  45
Leu Asn Leu Trp Ala Lys His Gly Thr Ser Glu Pro Val Ile Ala Phe
        50                  55                  60
Ala Gly His Thr Asp Val Val Pro Thr Gly Asp Glu Asn Gln Trp Ser
65                  70                  75                  80
Ser Pro Pro Phe Ser Ala Glu Ile Ile Asp Gly Met Leu Tyr Gly Arg
                85                  90                  95
```

-continued

```
Gly Ala Ala Asp Met Lys Gly Ser Leu Ala Ala Met Ile Val Ala Ala
            100                 105                 110

Glu Glu Tyr Val Lys Ala Asn Pro Asn His Lys Gly Thr Ile Ala Leu
        115                 120                 125

Leu Ile Thr Ser Asp Glu Ala Thr Ala Lys Asp Gly Thr Ile His
    130                 135                 140

Val Val Glu Thr Leu Met Ala Arg Asp Glu Lys Ile Thr Tyr Cys Met
145                 150                 155                 160

Val Gly Glu Pro Ser Ser Ala Lys Asn Leu Gly Asp Val Val Lys Asn
                165                 170                 175

Gly Arg Arg Gly Ser Ile Thr Gly Asn Leu Tyr Ile Gln Gly Ile Gln
            180                 185                 190

Gly His Val Ala Tyr Pro His Leu Ala Glu Asn Pro Ile His Lys Ala
        195                 200                 205

Ala Leu Phe Leu Gln Glu Leu Thr Thr Tyr Gln Trp Asp Lys Gly Asn
    210                 215                 220

Glu Phe Phe Pro Pro Thr Ser Leu Gln Ile Ala Asn Ile His Ala Gly
225                 230                 235                 240

Thr Gly Ser Asn Asn Val Ile Pro Ala Glu Leu Tyr Ile Gln Phe Asn
                245                 250                 255

Leu Arg Tyr Cys Thr Glu Val Thr Asp Glu Ile Ile Lys Gln Lys Val
            260                 265                 270

Ala Glu Met Leu Glu Lys His Asn Leu Lys Tyr Arg Ile Glu Trp Asn
        275                 280                 285

Leu Ser Gly Lys Pro Phe Leu Thr Lys Pro Gly Lys Leu Leu Asp Ser
    290                 295                 300

Ile Thr Ser Ala Ile Glu Glu Thr Ile Gly Ile Thr Pro Lys Ala Glu
305                 310                 315                 320

Thr Gly Gly Gly Thr Ser Asp Gly Arg Phe Ile Ala Leu Met Gly Ala
                325                 330                 335

Glu Val Val Glu Phe Gly Pro Leu Asn Ser Thr Ile His Lys Val Asn
            340                 345                 350

Glu Glu Glu
        355

<210> SEQ ID NO 29
<211> LENGTH: 388
<212> TYPE: PRT
<213> ORGANISM: H. pylori

<400> SEQUENCE: 29

Met Asn Ala Leu Glu Ile Thr Gln Lys Leu Ile Ser Tyr Pro Thr Ile
1               5                   10                  15

Thr Pro Lys Glu Cys Gly Ile Phe Glu Tyr Ile Lys Ser Leu Phe Pro
            20                  25                  30

Ala Phe Lys Thr Leu Glu Cys Gly Glu Asn Gly Val Lys Asn Leu Phe
        35                  40                  45

Leu Tyr Arg Ile Phe Asn Pro Lys Glu His Ala Glu Lys Glu His
    50                  55                  60

Ala Lys Glu Lys His Ala Lys Glu Asn Val Lys Pro Leu His Phe Ser
65                  70                  75                  80

Phe Ala Gly His Ile Asp Val Val Pro Pro Gly Asp Asn Trp Gln Ser
                85                  90                  95

Asp Pro Phe Lys Pro Ile Ile Lys Glu Gly Phe Leu Tyr Gly Arg Gly
            100                 105                 110
```

```
Ala Gln Asp Met Lys Gly Gly Val Gly Ala Phe Leu Ser Ala Ser Leu
        115                 120                 125

Asn Phe Asn Pro Lys Thr Pro Phe Leu Leu Ser Ile Leu Leu Thr Ser
        130                 135                 140

Asp Glu Glu Gly Pro Gly Ile Phe Gly Thr Lys Leu Met Leu Glu Lys
145                 150                 155                 160

Leu Lys Glu Lys Asp Leu Leu Pro His Met Ala Ile Val Ala Glu Pro
                165                 170                 175

Thr Cys Glu Lys Val Leu Gly Asp Ser Ile Lys Ile Gly Arg Arg Gly
        180                 185                 190

Ser Ile Asn Gly Arg Leu Ile Leu Lys Gly Val Gln Gly His Val Ala
        195                 200                 205

Tyr Pro Gln Lys Cys Gln Asn Pro Ile Asp Thr Leu Ala Ser Val Leu
        210                 215                 220

Pro Ser Ile Ser Gly Val His Leu Asp Asp Gly Asp Glu Tyr Phe Asp
225                 230                 235                 240

Pro Ser Lys Leu Val Val Thr Asn Leu His Ala Gly Leu Gly Ala Asn
                245                 250                 255

Asn Val Thr Pro Gly Ser Val Glu Ile Thr Phe Asn Ala Arg His Ser
        260                 265                 270

Leu Lys Thr Thr Lys Glu Ser Leu Lys Glu Tyr Leu Glu Lys Val Leu
        275                 280                 285

Lys Asp Leu Pro His Thr Leu Glu Leu Glu Ser Ser Ser Pro Phe
        290                 295                 300

Ile Thr Ala Ser His Ser Lys Leu Thr Ser Val Leu Lys Glu Asn Ile
305                 310                 315                 320

Leu Lys Thr Cys Arg Thr Thr Pro Leu Leu Asn Thr Lys Gly Gly Thr
                325                 330                 335

Ser Asp Ala Arg Phe Phe Ser Ala His Gly Ile Glu Val Val Glu Phe
        340                 345                 350

Gly Val Ile Asn Asp Arg Ile His Ala Ile Asp Glu Arg Val Ser Leu
        355                 360                 365

Lys Glu Leu Glu Leu Leu Glu Lys Val Phe Leu Gly Val Leu Glu Gly
        370                 375                 380

Leu Ser Glu Ala
385

<210> SEQ ID NO 30
<211> LENGTH: 370
<212> TYPE: PRT
<213> ORGANISM: E. coli

<400> SEQUENCE: 30

Met Ser Cys Pro Val Ile Glu Leu Thr Gln Gln Leu Ile Arg Arg Pro
 1               5                  10                  15

Ser Leu Ser Pro Asp Asp Ala Gly Cys Gln Ala Leu Leu Ile Glu Arg
                20                  25                  30

Leu Gln Ala Ile Gly Phe Thr Val Glu Arg Met Asp Phe Ala Asp Thr
            35                  40                  45

Gln Asn Phe Trp Ala Trp Arg Gly Gln Gly Glu Thr Leu Ala Phe Ala
        50                  55                  60

Gly His Thr Asp Val Val Pro Pro Gly Asp Ala Asp Arg Trp Ile Asn
65                  70                  75                  80

Pro Pro Phe Glu Pro Thr Ile Arg Asp Gly Met Leu Phe Gly Arg Gly
```

-continued

```
                            85                      90                      95
Ala Ala Asp Met Lys Gly Ser Leu Ala Ala Met Val Val Ala Ala Glu
                100                     105                     110
Arg Phe Val Ala Gln His Pro Asn His Thr Gly Arg Leu Ala Phe Leu
                115                     120                     125
Ile Thr Ser Asp Glu Glu Ala Ser Ala His Asn Gly Thr Val Lys Val
                130                     135                     140
Val Glu Ala Leu Met Ala Arg Asn Glu Arg Leu Asp Tyr Cys Leu Val
145                     150                     155                     160
Gly Glu Pro Ser Ser Ile Glu Val Val Gly Asp Val Val Lys Asn Gly
                    165                     170                     175
Arg Arg Gly Ser Leu Thr Cys Asn Leu Thr Ile His Gly Val Gln Gly
                180                     185                     190
His Val Ala Tyr Pro His Leu Ala Asp Asn Pro Val His Arg Ala Ala
                195                     200                     205
Pro Phe Leu Asn Glu Leu Val Ala Ile Glu Trp Asp Gln Gly Asn Glu
            210                     215                     220
Phe Phe Pro Ala Thr Ser Met Gln Ile Ala Asn Ile Gln Ala Gly Thr
225                     230                     235                     240
Gly Ser Asn Asn Val Ile Pro Gly Glu Leu Phe Val Gln Phe Asn Phe
                    245                     250                     255
Arg Phe Ser Thr Glu Leu Thr Asp Glu Met Ile Lys Ala Gln Val Leu
                260                     265                     270
Ala Leu Leu Glu Lys His Gln Leu Arg Tyr Thr Val Asp Trp Trp Leu
            275                     280                     285
Ser Gly Gln Pro Phe Leu Thr Ala Arg Gly Lys Leu Val Asp Ala Val
        290                     295                     300
Val Asn Ala Val Glu His Tyr Asn Glu Ile Lys Pro Gln Leu Leu Thr
305                     310                     315                     320
Thr Gly Gly Thr Ser Asp Gly Arg Phe Ile Ala Arg Met Gly Ala Gln
                    325                     330                     335
Val Val Glu Leu Gly Pro Val Asn Ala Thr Ile His Lys Ile Asn Glu
                340                     345                     350
Cys Val Asn Ala Ala Asp Leu Gln Leu Gln Arg Ile Met Glu Gln Leu
                355                     360                     365

Val Ala
    370
```